(12) United States Patent
Schmaier et al.

(10) Patent No.: US 7,879,792 B2
(45) Date of Patent: Feb. 1, 2011

(54) SYNTHETIC PEPTIDE INHIBITORS OF THROMBIN AND THROMBIN ACTIVATION OF PROTEASE ACTIVATED RECEPTORS 1 AND 4

(75) Inventors: Alvin H. Schmaier, Ann Arbor, MI (US); Henry I. Mosberg, Ann Arbor, MI (US); Fernanda F. Marques, Ann Arbor, MI (US); John Hilfinger, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1520 days.

(21) Appl. No.: 11/142,364

(22) Filed: Jun. 2, 2005

(65) Prior Publication Data

US 2006/0276402 A1    Dec. 7, 2006

(51) Int. Cl.
*A61K 38/00* (2006.01)
*A61K 38/04* (2006.01)
*A61K 38/36* (2006.01)

(52) U.S. Cl. .......................... 514/1.1; 514/17; 530/330; 424/94.64

(58) Field of Classification Search ...................... None
See application file for complete search history.

(56) References Cited

U.S. PATENT DOCUMENTS

| 6,143,719 | A  | * | 11/2000 | Schmaier et al. | .............. | 514/12 |
| 7,074,765 | B2 | * | 7/2006  | Schmaier et al. | .............. | 514/12 |
| 2004/0220110 | A1 | * | 11/2004 | Schmaier et al. | .............. | 514/17 |

OTHER PUBLICATIONS

Hasan, 2001, Thrombosis Research, 104, 451-465.*
Thurieau et al. "Design and Synthesis of New Linear and Cyclic Bradykinin Antagonists", Journal of Medicinal Chemistry, 1996, 2095-2101, 39.

* cited by examiner

*Primary Examiner*—Cecilia Tsang
*Assistant Examiner*—Satyanarayana R Gudibande
(74) *Attorney, Agent, or Firm*—Marshall, Gerstein & Borun LLP

(57) ABSTRACT

The invention relates to synthetic peptide analogs of D-Arg-Oic-Pro-Gly-Phe and methods of their use to inhibit human platelet aggregation, thrombosis and cell activation mediated by PAR1 and PAR4.

38 Claims, 12 Drawing Sheets

US 7,879,792 B2

SYNTHETIC PEPTIDE INHIBITORS OF THROMBIN AND THROMBIN ACTIVATION OF PROTEASE ACTIVATED RECEPTORS 1 AND 4

REFERENCE TO GOVERNMENT GRANT

The invention described herein was made, in part, in the course of work supported by the National Heart Lung and Blood Institute under Grant Nos. HL61981, HL75229 and the Michigan Life Science Corridor Proposal #1607. The government has certain rights in the invention.

FIELD OF INVENTION

This invention relates to synthetic peptide analogs of D-Arg-Oic-Pro-Gly-Phe for inhibiting human platelet aggregation, thrombosis and cell activation mediated by PAR1 and PAR4.

BACKGROUND OF THE INVENTION

Bradykinin (Arg-Pro-Pro-Gly-Phe-Ser-Pro-Phe-Arg, SEQ ID NO:1) is a vasoactive peptide released from the precursor plasma kininogens by plasma and tissue kallikreins and other enzymes (Silva et al., *Amer. J. Physiol.* 156: 261-274 (1949)). The parent proteins of bradykinin, high (HK) and low (LK) molecular weight kininogens are recognized to have the ability to inhibit α- and γ-thrombin-induced platelet activation (Meloni et al., *J. Biol. Chem.* 266, 6786 (1991); Puri et al., *Blood* 77, 500 (1991)). Both low and high molecular weight kininogens have identical amino acid sequences from their amino-terminus through 12 amino acids beyond the carboxy-terminus of bradykinin. Both LK and HK share a common heavy chain (62 kDa), the bradykinin (BK) moiety (0.9 kDa), and the first 12 amino acids of the amino terminal portion of each of their "light chains" (Takagaki et al., *J. Biol. Chem.* 260, 8601-8609 (1985); Kitamura et al., *J. Biol. Chem.*, 260, 8610-8617 (1985)). This identity corresponds to residues 1 through about residue 383 (See Salveson et al., *Biochem J.* 243, 429 (1986); Kellerman et al., *Eur. J. Biochem.* 154, 471 (1986)). The HK and LK kininogens diverge in the size of their light chains; the light chain of LK is 4 kDa; that of HK is 56 kDa. (Takagaki et al., supra; Kitamura et al., supra.). The kininogens prevent thrombin-induced platelet activation. Full-length kininogens prevent thrombin from binding to platelets. Thus, the prior art indicated that kininogens' ability to inhibit thrombin activation of platelets was more than direct interaction with the thrombin molecule itself (Meloni et al., supra; Puri et al., supra).

The thrombin inhibitory activity of the kininogens was thought to be localized to an isolated domain 3 of the kininogens' heavy chain, because domain 3 retained all the thrombin inhibitory activity of the whole protein (Jiang et al., *J. Biol. Chem.* 267, 3712 (1992)). The thrombin inhibitory activity of the kininogens was later found to be associated with domain 4, the bradykinin sequence, which was attached to the carboxyterminal end of isolated domain 3 prepared by proteolytic cleavage of whole LK (Hasan et al., *Circulation* 94, 517-528 (1996); Tayeh et al., *J. Biol. Chem.* 269, 16318-16325 (1994)). Bradykinin, itself, has been recognized to antagonize the effects of α-thrombin (Ehringer et al., *Inflammation.* 21:279-298 (1997)). The thrombin inhibitory region of domain 4, the bradykinin sequence, demonstrated a number of features. This sequence did not prevent thrombin from binding to platelets and it did not prevent the thrombin receptor activation peptide (TRAP), SFLLRN (Ser-Phe-Leu-Leu-Arg-Asn, SEQ ID NO:2), from stimulating calcium mobilization and platelet aggregation in platelets. This sequence from domain 4 prevented thrombin-activated platelets from losing an epitope to monoclonal antibody SPAN12. Monoclonal antibody SPAN12 is directed to the thrombin cleavage site on protease activated receptor 1 (PAR1) (Hasan et al., supra; Vu et al., *Cell* 64, 1057-1068 (1991); Brass et al., *J. Biol. Chem.* 267, 13795-13798 (1992)). Monoclonal antibody SPAN12 was raised to the peptide NATLDPRSFLLR (Asn-Ala-Thr-Leu-Asp-Pro-Arg-Ser-Phe-Leu-Leu-Arg, SEQ ID NO:3) (Brass et. al., supra.). Further, bradykinin analog peptides prevented α-thrombin from cleaving the peptide NATLDPRSFLLR (SEQ ID NO:3) between arginine and serine, the identical place on PAR1 that thrombin cleaves to activate this receptor. Although there are a number of peptide analogs of bradykinin that demonstrate thrombin inhibiting activity against platelet activation, the minimal sequences retaining this activity are the peptides, RPPGF (Arg-Pro-Pro-Gly-Phe, SEQ ID NO:4), RPPG (Arg-Pro-Pro-Gly, SEQ ID NO:5), and RPP (Arg-Pro-Pro). FITC-labeled (fluorescein isothiocyanate) RPPGF (SEQ ID NO: 4) has the ability to directly bind to platelets (Hasan et al., *Thromb Haemost.* 82, 1182-1187 (1999)). These data indicate that the RPPGF (SEQ ID NO:4) and related bradykinin analog peptides have the ability to bind to platelets to prevent thrombin-induced platelet activation. RPPGF (SEQ ID NO:4) and its related peptide, MAP4-RPPGF (β-Ala-Lys-2Lys-4(Arg-Pro-Pro-Gly-Phe)) (RPPGF disclosed as SEQ ID NO: 4) have the ability to interfere with α- or γ-thrombin-induced platelet activation two ways: at high concentrations these peptides are retrobinders to the active site of thrombin ($K_i$=1.75 mM). At lower concentrations they bind to protease activated receptor 1 (PAR1) near the thrombin cleavage site to prevent thrombin cleavage of the extracellular domain of PAR1 (Hasan et al., *Blood.* 98, 530a, (2001); Hasan et al. *Amer J Physiol. Heart Circ Physiol.* 285, H183, (2003)). Bradykinin, itself, has been shown to be a direct inhibitor of thrombin with a $K_i$ between 170 to 326 μM (Cleary et al., *Arch. Biochem. Biophys.* 410, 96-106 (2003)). Furthermore, rOicPGF and MAP4-rOicPGF (β-Ala-Lys-2Lys-4(rOicPGF)) inhibit the enzymatic activity of α-thrombin and factor VIIa (Nieman et al. *J. Pharm Exp Therap.* 311, 492 (2004)). Thrombin has two binding sites on PAR1. It binds by its exosite I region to a hirugen-like region on the carboxyterminus of the extracellular fragment of PAR1 which includes the amino acid sequence Asp-Lys-Tyr-Glu-Pro-Phe-Trp-Glu-Asp-Glu-Glu-Lys (SEQ ID NO:6) (Ayala et al. *Proteins:Structure, Function, and Genetics.* 45, 107-116 (2001)). It also binds to a region adjacent to the thrombin cleavage site on PAR1, the sequence Leu-Asp-Pro-Arg (SEQ ID NO:7) (Ayala et al. *Proteins:Structure, Function, and Genetics.* 45, 107-116 (2001)). Alternatively, when thrombin cleaves PAR4, it only binds to a region adjacent to the thrombin cleavage site Leu-Pro-Ala-Pro-Arg (SEQ ID NO:8) (Ayala et al. *Proteins:Structure, Function, and Genetics.* 45, 107-116 (2001)). On human PAR4, there is no equivalent hirugen binding region as seen on PAR1 on the extracellular fragment of PAR4. Both RPPGF (SEQ ID NO:4) and rOicPGF prevent RPPGFK-biotin (SEQ ID NO: 15) from binding to a peptide (Ser-Ile-Leu-Pro-Ala-Pro-Arg-Gly-Tyr-Pro-Gly-Gln, (SEQ ID NO:9)) of the thrombin cleavage site on the exodomain of human protease activated receptor 4 (PAR4) (Nieman et al. *FEBS Letters,* 579, 25, (2005)). RPPGF (SEQ ID NO:4) binds via its arginine to the exodomain of human PAR4 to prevent thrombin cleavage (Nieman et al. *FEBS Letters,* 579, 25, (2005)). If proline 46 on the exodomain of PAR4 is changed to an alanine, RPPGF (SEQ ID NO:4) does not bind to the recombinant protein (Nieman et al. *FEBS Letters*, 579, 25, (2005)). This information indicates that the arginine on RPPGF (SEQ ID NO:4) specifically binds to Pro46 on the exodomain of human PAR4 to prevent α-thrombin cleavage (Nieman et al. *FEBS Letters*, 579, 25, (2005)).

The importance of the use of RPPGF (SEQ ID NO:4) and related compounds has been shown in animal studies. RPPGF (SEQ ID NO:4) prevents coronary thrombosis in the canine electrolytic injury model similar to aspirin treatment (Hasan et al. *Thrombosis and Haemostasis* 82, 1182-1187 (1999)). MAP4-RPPGF (β-Ala-Lys-2Lys-4(Arg-Pro-Pro-Gly-Phe)) (RPPGF disclosed as SEQ ID NO: 4) prevents cyclic flow variations in the Folt's model for canine coronary thrombosis to a similar degree as aspirin or clopidogrel (Hasan et al. *Thrombosis and Haemostasis* 86, 1296-1304 (2001)). RPPGF (SEQ ID NO:4) infusion delays the time to death in lipopolysaccharide-treated rats (Morinelli et al. *J. Pharm Exp. Ther.* 296, 71-76 (2001)). RPPGF (SEQ ID NO:4) reduced platelet activation and deposition in an ex vivo model of balloon injury to the vessel wall similar to the effects of aspirin (Prieto et al. *Cardiovascular Research*. 53, 984-992 (2001)). Finally, MAP4-RPPGF (RPPGF disclosed as SEQ ID NO: 4) delays the time to thrombosis of the mouse carotid artery and inhibits mouse platelet aggregation (Srikanth et al. *Blood*. 100, 24a, (2002), Nieman et al. *J. Pharm Exp Therap.* 311, 492 (2004)).

More physiologic investigations have been performed on RPPGF (SEQ ID NO:4). RPPGF (SEQ ID NO:4) has been recognized as the terminal breakdown product of angiotensin converting enzyme (Kuoppala et al. *Am J Physiol Heart Circ Physiol*. 278, H1069 (2000), Murphey et al. *J Pharm Exp Therap*. 294, 263 (2000), Murphey et al. *Anal Biochem*. 292, 87 (2001)). Infusion of RPPGF (SEQ ID NO:4) into rats ameliorated the deleterious effects of lipopolysaccharide (Morinelli et al. *J Pharm Exp Therap.* 296, 71 (2001)). Furthermore, treatment of rats with RPPGF (SEQ ID NO:4) resulted in reduction of local thrombin-induced edema in their brains (Jiang et al. *J. Cerebral Blood Flow & Metabolism*. 22, 404 (2002)). RPPGF (SEQ ID NO:4) and its analog rOicPGF block biotin-RPPGF (SEQ ID NO:4) from binding to a recombinant exodomain of human protease activated receptor 1 (Nieman et al. *J Pharm Exp Therap.* 311, 492 (2004)). D-Arginine-Oic-Pro-Gly-Phe inhibits thrombin-induced mouse platelet aggregation, prolongs mouse bleeding times, and inhibits mouse carotid artery thrombosis (Nieman et al. *J. Pharm Exp Therap.* 311, 492 (2004)).

The present invention relates to inhibition of thrombin-induced activation in human cells. Inhibition of thrombin activation of platelets or other cells can be either through an inhibitor of thrombin directed to the thrombin molecule itself or an inhibitor directed to substrates of thrombin. PAR1 and PAR4 (Xu et al. *Proc. Natl. Acad. Sci.* 95, 6642, (1998) are specific substrates of thrombin to which this class of inhibitors are directed. The present invention is directed to inhibition of activation of these thrombin substrates on any cell that expresses PAR1 or PAR4. These cells include normal platelets, endothelial cells, smooth muscle cells, fibroblasts, neuronal cells, or any other normal or cancerous cell that contains these receptors. U.S. patent application Ser. No. 10/426,968, filed May 1, 2003 describes selective peptide inhibitors of thrombin and activation of PAR1 and PAR4.

The following abbreviations have been used:

A: any naturally occurring amino acid or a synthetic amino acid as shown in Table I BK: bradykinin (Arg-Pro-Pro-Gly-Phe-Ser-Pro-Phe-Arg, SEQ ID NO:1);

D3: domain 3 of kininogens;

D4: domain 4 of kininogen that is the bradykinin region;

FITC: fluorescein isothiocyanate;

HK: high molecular weight kininogen;

LK: low molecular weight kininogen;

MAP4-RPPGF: A four-branched peptide consisting of a β-alanine core with a single lysine attached at its amino terminal end followed by two additional lysines. Each lysine will then have two RPPGF (SEQ ID NO:4) peptides attached by the phenylalanine to each of the lysines;

NAT12: peptide sequence Asn-Ala-Thr-Leu-Asp-Pro-Arg-Ser-Phe-Leu-Leu-Arg (SEQ ID NO:3) that spans the α-thrombin cleavage site on the thrombin receptor;

SIL12 peptide sequence Ser-Ile-Leu-Pro-Ala-Pro-Arg-Gly-Tyr-Pro-Gly-Gln (SEQ ID NO:9) that spans the α- and γ-thrombin cleavage site on the thrombin receptor.

PAR1: protease activated receptor 1;

PAR4 protease activated receptor 4;

PTCA: percutaneous transluminal coronary angioplasty;

RPPGF: Arg-Pro-Pro-Gly-Phe (SEQ ID NO:4);

RPPGC: Arg-Pro-Pro-Gly-Cys (SEQ ID NO:10)

rOicPGF: D-Arg-Oic-Pro-Gly-Phe;

MAP4-rOicPGF: β-Ala-Lys-2Lys-4(D-Arg-Oic-Pro-Gly-Phe);

FPRPG: Phe-Pro-Arg-Pro-Gly (SEQ ID NO:11)

SPAN12: a monoclonal antibody specific for the sequence Asn-Ala-Thr-Leu-Asp-Pro-Arg-Ser-Phe-Leu-Leu-Arg (SEQ ID NO:3) that spans the α-thrombin cleavage site on PAR1; and X: nomenclature for one of eight synthetic amino acids Z: nomenclature for any naturally occurring amino acid.

APTT activated partial thromboplastin time, an assay to measure the clotting of plasma.

PT prothrombin time, an assay to measure the clotting of plasma

TCT thrombin clotting time, an assay to measure the integrity of fibrinogen in plasma or with purified fibrinogen

SUMMARY OF THE INVENTION

The invention relates to a series of compounds to inhibit thrombin-induced platelet or human cell activation, and to methods of inhibiting thrombin-mediated activities. In one aspect, the invention includes a peptide that inhibits thrombin activation of platelets or human cells, wherein said peptide comprises a naturally occurring or synthetic (unnatural) amino acid sequence of the formula:

$$A_1\text{-}A_2\text{-}A_3\text{-}A_4\text{-}A_5 \tag{I}$$

wherein:

each of $A_{1\text{-}5}$ is independently one of 8 unnatural amino acid residues from Table II, one of 20 natural amino acid residues set forth in TABLE I, or is a D amino acid residue from Table II. Preferably, $A_1\text{-}A_2\text{-}A_3\text{-}A_4\text{-}A_5$ contains at least one non-naturally occurring amino acid and more preferably it contains no naturally occurring peptide bonds. (As used herein, a "naturally occurring peptide bond" is one that occurs between two naturally occurring amino acid residues.) In one preferred embodiment, $A_1\text{-}A_2\text{-}A_3\text{-}A_4\text{-}A_5$ is located at the N-terminus of the peptide.

The invention also includes a method for inhibiting thrombin mediated activities including, but not limited to, thrombin-induced platelet aggregation, thrombin-induced calcium mobilization, thrombin-induced cell motility, coagulation, cell adhesion, and other such activities described herein, by administering an effective amount of a compound of the invention, as described hereinabove, or below.

As used herein, "effective amount" means an amount sufficient to produce a measurable response.

TABLE I

Naturally Occurring Amino Acids

| Amino Acid | Three-letter abbreviation | One-letter symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE II

Synthetic Amino Acids Used to Prepare Peptides

| Amino Acid | 3 Letter Abbreviation | letter symbol |
|---|---|---|
| D-arginine | D-Arg | r |
| D-alanine | D-Ala | a |
| D-serine | D-Ser | s |
| (2S,3aS,7aS)-octahydroindole-2-carboxlic acid | Oic | — |
| phenylalanine(para-methyl) | — | (p-Me)F |
| phenylalanine(para-bromo) | — | (p-Br)F |
| phenylalanine(para-iodo) | — | (p-I)F |
| phenylalanine(para-nitro) | — | (p-NO$_2$)F |

In a preferred embodiment, the peptide comprises a peptide compound $A_1$-$A_2$-$A_3$-$A_4$-$A_5$ wherein:
$A_1$ is D-arginine (r);
$A_2$ is (2S, 3aS, 7aS)-octahydroindole-2-carboxlic acid (Oic);
$A_3$ is L-proline (P);
$A_4$ is selected from the group consisting of D-alanine (a) and D-serine (s);
$A_5$ is selected from the group consisting of L-phenylalanine with a methyl group attached at the para position of the side chain aromatic ring (Phe(p-Me)) (F(p-Me)), L-phenylalanine with a bromo group attached at the para position of the side chain aromatic ring (Phe(p-Br)) (F(p-Br)), L-phenylalanine with an iodo group attached at the para position of the side chain aromatic ring (Phe (p-I)), (F(p-I)), and L-phenylalanine with a nitro group attached at the para position of the side chain aromatic ring (Phe(p-NO$_2$)), (F(p-NO$_2$)).

Preferably said compound contains 28 or fewer, more preferably 10 or fewer, amino acid residues.

In other preferred embodiments, one or two substitutions are made to parent compound RPPGF (SEQ ID NO: 4). In a particularly preferred embodiment, $A_1$ is D-Arg. In one particularly preferred embodiment, the pentapeptide includes at least 4 non-naturally-occurring amino acid residues.

The peptides of the invention also include derivatives and analogs of these peptides, having modifications such as blocking groups (especially amidation at the C-terminus, but including, for example blocking groups on the C-terminus, N-terminus, and any charged side chains). Such groups may be added, for example, by amidation, esterification, and other means well known in the art. Such modifications are expected to enhance absorption and increase therapeutic efficacy of the compounds. Examples of blocking groups are NH$_2$, lower alkyl or alkoxy(C$_1$-C$_6$), lower alkyl carbonyl, lower alkenyl, lower alkynyl, formyl, lower aryl, aroyl, aryloxy-carbonyl, aralkyloxy-carbonyl, lower alkyloxycarbonyl, phenyl, benzoyl, polyethylene glycol, nitro, —CN, saccharides, reduced carboxylates (i.e. aldehyde and alcohol), hydrazide, higher alkyl acylation (e.g. fatty acid acylation), biotinylation, and fluorescent labels. In all instances, "lower" refers to carbon chains having 1-6 carbon atoms. Persons of skill in the art will be familiar with the methods for making such modifications (see, e.g. Richard C. Larock, "Comprehensive Organic Transformations", 2nd Edition, published by Wiley-VCH. 1999.)

Analogs of the invention also include MAP4-$A_1$-$A_2$-$A_3$-$A_4$-$A_5$, a four-branched peptide consisting of a β-alanine core with a single lysine attached at its amino terminal end followed by two additional lysines. Each lysine will then have two $A_1$-$A_2$-$A_3$-$A_4$-$A_5$ peptides attached by the phenylalanine to each of the lysines. For example, MAP4-rOicPaF(p-Me) is a multiantigenic peptide consisting of a Lys-β-alanine core with two lysines attached to the 2 free amino groups on the first lysine and four molecules of rOicPaF(p-Me) attached to the two free amino groups on the second lysine. Similar MAP compounds can be made with other peptides of the invention and are expected to inhibit thrombin-mediated activities as described herein below for the peptides themselves.

In one embodiment, the invention comprises treating platelets or human cells with a compound of Formula I, or an analog or derivative thereof, to inhibit thrombin activation of platelets or activation of other cells, which express the thrombin receptors PAR1 or PAR4. Some of the preferred compounds include D-Arg-Oic-Pro-D-Ala-Phe(p-Me), D-Arg-Oic-Pro-D-Ser-Phe(p-Me), D-Arg-Oic-Pro-D-Ala-Phe(p-Br), D-Arg-Oic-Pro-D-Ala-Phe(p-I), and D-Arg-Oic-Pro-D-Ala-Phe(p-NO$_2$).

An object of administration of these peptides of Formula I, and analogs and derivatives thereof, to cells is to prevent thrombosis, i.e., an occlusion of a vessel due to formation of a platelet-rich, fibrin-rich or a mixed platelet-fibrin thrombus. Accordingly, the invention relates to the foregoing compounds, derivatives and analogs, and to the contact of these compounds, derivatives and analogs with platelets and human cells which express the thrombin receptor to prevent thrombosis. Another object of this invention is to inhibit cancer cell growth, invasion, or metastasis where the thrombin receptors PAR and/or PAR4 are expressed. Further, this invention could be used to prevent brain edema due to the presence of thrombin.

Included in the invention are methods of inhibiting thrombin-mediated activities comprising administration of the compounds of Formula I, and analogs and derivatives thereof to cells and animals in vitro and in vivo. Such activities include, inter alia, thrombin-induced platelet aggregation, thrombin-induced calcium mobilization, thrombin-mediated coagulation, thrombin-induced cell motility, and thrombin-induced cell adhesion. The compounds and methods of the invention are particularly relevant for use in humans and other mammals. Further, this invention shows how the compounds in the present invention inhibit RPPGFK-biotin (SEQ ID NO: 15) from binding to recombinant exodomain from PAR1 or PAR4 linked to microtiter plates. These investigations also show how the present compounds inhibit human α-thrombin from hydrolyzing a chromogenic substrate of thrombin. The results presented herein show that these compounds are stable in an intestinal perfusate and homogenate. Further, these compounds are permeable in an in situ perfusion. This information indicates that the compounds of the invention are taken-up by cells that express the gut di- and tripeptide transporter systems. Thus, the compounds of the invention have the potential for oral delivery.

In another aspect, the invention includes tripeptides and tetrapeptides of formula $A_1$-$A_2$-$A_3$-$A_4$, wherein
$A_1$ is D-arginine (r) or L-arginine;
$A_2$ is (2S, 3aS, 7aS)-octahydroindole-2-carboxlic acid (Oic) or L-Proline;
$A_3$ is Oic or L-proline; and
$A_4$, when present, is selected from the group consisting of D-alanine (a) and D-serine (s).

Preferably such tri- and tetrapeptides include at least one non-natural amino acid residue, and contain no naturally occurring peptide bonds. The invention also includes methods for using such tri- and tetrapeptides for anti-thrombin purposes, as described above. These compounds also show good oral absorption, inhibit thrombin mediated activities, and are suitable for therapeutic purposes.

DETAILED DESCRIPTION OF THE INVENTION

Definitions

Figure 1:
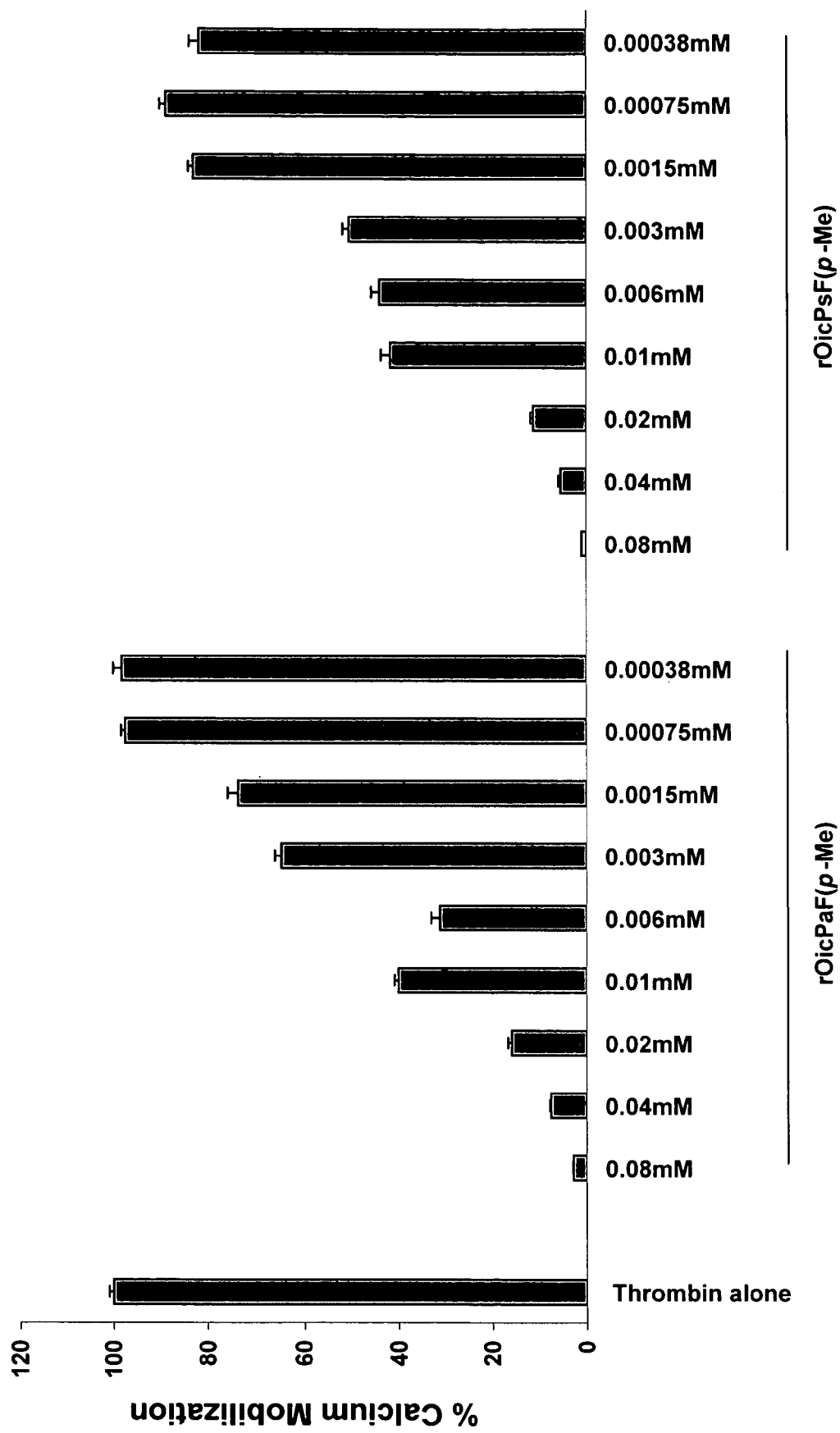
FIG. 1 illustrates the effect of the peptides rOicPaF(p-Me) and rOicPsF(p-Me) on α-thrombin-induced calcium mobilization in normal human lung fibroblasts. Two nM alpha thrombin was able to stimulate maximal calcium flux (Thrombin alone). When 0.08 mM of rOicPaF(p-Me) or rOicPsF(p-Me) was present, there was 97% inhibition of thrombin-induced calcium mobilization. As the concentration of rOicPaF(p-Me) and rOicPsF(p-Me) were decreased from 0.08 mM to 0.003 mM, there was decreased inhibition of thrombin-induced calcium mobilization to 69% and 59%, respectively. At 0.00038 mM rOicPaF(p-Me) and rOicPsF(p-Me), there was full recovery of alpha thrombin-induced calcium mobilization.

"Natural amino acid" means any of the twenty primary, naturally occurring amino acids which typically form peptides, polypeptides, and proteins.

Table I is a tabulation of 20 naturally occurring amino acids.

"Synthetic amino acid" means any other amino acid, regardless of whether it is prepared synthetically or derived from a natural source. As used herein, "synthetic amino acid" also encompasses chemically modified amino acids, including but not limited to salts, derivatives (such as amides), and substitutions.

The invention relates to the peptides, derivatives and analogs of Formula I above. Peptides of the invention can be produced by conventional solid phase peptide synthesis techniques using automated synthesis.

The general approach for the preparation of these peptides is to substitute non-natural amino acids for natural amino acids to create compounds that are not metabolized as peptides with naturally occurring amino acids.

Peptide analogs of RPPGF (Arg-Pro-Pro-Gly-Phe, SEQ ID NO:4) were prepared by traditional solid-phase peptide synthesis (Merrifield R B. *J. Amer. Chem. Soc.* 85, 2149-2154 (1963)) on Applied Biosystems, Inc. synthesizer model 431A. The peptides were assembled on peptide amide linker polyethylene glycol polystyrene resin (PAL-PEG-PS resin) using traditional Fmoc based chemistry. The amide resin was used in order to obtain a carboxamide at the C-terminus of the peptide. The protected amino acids were Fmoc-D-Arg (Pbf), Fmoc-Phe(p-Me), Fmoc-Phe(p-Br), Fmoc-Phe(p-I), Fmoc-Phe(p-NO$_2$), Fmoc-Pro, Fmoc-Oic, Fmoc-D-Ser(tBu), and Fmoc-D-Ala with Fmoc being 9-fluorenylmethyloxycarbonyl, Oic being octahydroindole-2-carboxylic acid, tBu being t-butyl ether, and Pbf being 2,2,4,6,7-pentamethyl-dihydrobenzofuran-5-sulfonyl.

The synthesis occurs in a cycle that is initiated by the swelling of the resin (0.25 mmol) in dichloromethane (DCM) followed by the removal of the Fmoc group of the resin with piperidine, to generate a free amine available for coupling with the C-terminal amino acid of the peptide sequence. This step is followed by extensive N-methylpyrrolidone (NMP) wash, and, subsequently, by coupling of the first (C-terminal) amino acid to the resin. Coupling is facilitated by o-benzotriazol-1-yl-N,N,N',N'-tetramethyl uronium hexafluorophosphate (HBTU), which is dissolved in a solution of 1-hydroxybenzotriazole (HOBt) and N,N-dimethylformamide (DMF). The amino acid is dissolved in the HBTU/HOBt solution along with additional NMP. The reaction is carried out in the presence of 2.0 M N,N-diisoproprylethylamine (DIEA), which creates the basic environment necessary for the activation of the amino acid residue (Fields C G. *Peptide Research* 4, 95-101 (1991)). The activated amino acid reacts with the deprotected amino-terminal of the growing peptide chain. The final step in the coupling cycle involves acetylation of unreacted amino groups by addition of 10-fold excess of 0.5 M acetic anhydride, 0.125 M DIEA, and 0.015 M HOBt in NMP. The above reactions are repeated for each amino acid in the peptide sequence, progressing from C-terminal to N-terminal. Once the fifth and final amino acid is added, the resin is filtered and washed with DCM and ethyl alcohol (EtOH) to complete the solid phase component of the synthesis.

Trifluoroacetic acid/H$_2$O/thioanisole/ethylenedithiol solution (9:0.5:0.25:0.25, v/v/v/v) is used to cleave the linear peptide from the resin and simultaneously remove the side chain protecting groups. The peptide solution is filtered from the resin and then subjected to preparative reverse-phase high-performance liquid chromatography (RP-HPLC) to afford the linear peptide. Final product confirmation is obtained by electrospray mass spectrometry (ThermoFinnigan, CA, USA).

The invention is directed, inter alia, to a method for preventing thrombosis using synthetic peptides, analogs and derivatives that act as selective antithrombins. These compounds are selective antithrombins because they are able to directly interact with human α-thrombin or γ-thrombin at their active site and are also able to inhibit human α-thrombin or γ-thrombin from cleaving PAR1 or PAR4 at its thrombin cleavage site to prevent thrombin induced stimulus-response coupling and activation of platelets and other normal or cancerous cells. These compounds bind to PAR1 at the sequence LDPR[41] (Leu-Asp-Pro-Arg, SEQ ID NO:7) or PRSF[43] (Pro-Arg-Ser-Phe, SEQ ID NO:12) and prevent thrombin from cleaving PAR1 between its Arg[41] and Ser[42] (Hasan et al. *Am J. Physiol. Heart Circ Physiol.* 285, H183, (2003)). These compounds also bind to human PAR4, probably to Pro[46] (Nieman et al., *FEBS Letters*, 579, 25 (2005)). The relative concentrations of thrombin to platelets used to induce platelet activation or aggregation ranged from about 0.25 to about 3 nM of α-thrombin or about 15 to 70 nM of γ-thrombin. Compounds of Formula I and analogs and derivatives thereof achieve selectivity in inhibiting thrombin activation by being directed to both a substrate of thrombin (PAR1 or PAR4) and the enzyme itself. Most known thrombin inhibitors, hirudin, hirugen, argatroban, bivalirudin interfere with α-thrombin's action only by interacting with thrombin itself at its active site and/or exosite I. Use of these known proteolytic inhibitors to block α- or γ-thrombin activation of platelets and other cells expressing PAR1 or PAR4 may result in excessive anticoagulation, hemorrhage, and interference with other important biologic activities such as mitogenesis and cell proliferation. The compounds utilized in the present method allow for inhibition of thrombin-induced platelet or other cell stimulus-response coupling and activation mediated by two substrates of thrombin, PAR1 and PAR4, without interfering with some of the other α-thrombin activities such as activation of factors V and XIII.

We have found that the compounds described herein bind to both PAR1 and PAR4 and inhibit thrombin cleavage of the thrombin receptors (PAR1 and PAR4) which are expressed on human platelets, fibroblasts and other normal or cancerous human cells. The compounds described herein also inhibit thrombin activation of mouse platelets—platelets that only express PAR4. Thus, we have found that the compounds described herein have the ability to inhibit thrombin-induced platelet activation by blocking thrombin itself and thrombin cleavage of PAR1 and PAR4 and subsequent activation of platelets by exposure of the new amino termini of these cleaved receptors. Administration of a compound described herein comprises a method for inhibiting thrombin-induced activation of platelets, endothelial cells, brain cells, fibroblasts, smooth muscle cells, or other normal or cancerous cells that contain the PAR1 and/or PAR4 receptor for thrombin. The activity of this inhibitor blocks platelet thrombus formation, calcium flux in many cells, and other activities mediated by the thrombin receptor.

The compounds described herein do not inhibit platelet activation by the same mechanism as intact kininogens or isolated domain 3. One mM peptide analogs do not block $^{125}$I-α-thrombin binding to platelets, as do molar excess purified HK, LK, or isolated domain 3. We have found that these peptide analogs:

1) block α-thrombin-induced calcium mobilization in fibroblasts;

2) block γ-thrombin-induced platelet aggregation in human platelets;

According to one embodiment of the invention, these compounds represent an amino acid substitution in any one or more of the five positions of the parent peptide so that the resulting compound exhibits the desired activity.

The following sequence of recombinant extracellular domain of PAR1 (rPAR1$_{EC}$) from alanine$^{26}$ to serine$^{99}$ was used to screen the present peptide antagonists:

(SEQ ID NO: 13)
Ala$^{26}$-Arg-Arg-Pro-Glu-Ser-Lys-Ala-Thr-Asn-Ala-Thr-

Leu-Asp-Pro-Arg-Ser-Phe-Leu-Leu-Arg-Asn-Pro-Asn-

Asp-Lys-Tyr-Glu-Pro-Phe-Trp-Glu-Asp-Glu-Glu-Lys-

Asn-Glu-Ser-Gly-Leu-Thr-Glu-Tyr-Arg-Leu-Val-Ser-

Ile-Asn-Lys-Ser-Ser-Pro-Leu-Gln-Lys-Gln-Leu-Pro-

Ala-Phe-Ile-Ser-Glu-Asp-Ala-Ser-Gly-Tyr-Leu-Thr-

Ser-Ser$^{99}$

This sequence was derived from Vu et al. *Cell* 64, 1057 (1991).

The following sequence of recombinant extracellular domain of PAR4 (rPAR4$_{EC}$) from glycine$^{18}$ to arginine$^{78}$ was also used to screen the present peptide antagonists:

(SEQ ID NO: 14)
Gly$^{18}$-Gly-Thr-Gln-Thr-Pro-Ser-Val-Tyr-Asp-Glu-Ser-

Gly-Ser-Thr-Gly-Gly-Gly-Asp-Asp-Ser-Thr-Pro-Ser-

Ile-Leu-Pro-Ala-Pro-Arg-Gly-Trp-Pro-Gly-Gln-Val-

Cys-Ala-Asn-Asp-Ser-Asp-Thr-Leu-Glu-Leu-Pro-Asp-

Ser-Ser-Arg-Ala-Leu-Leu-Leu-Gly-Trp-Val-Pro-Thr-

Arg$^{78}$

This sequence is from Xu et al. *Proc. Natl. Acad. Sci.* 95, 6642 (1998).

I. Preparation of Peptide Analogs that Interfere with Thrombin-Induced Platelet Aggregation A. Assays to Screen Peptide Libraries Nine assays were utilized to screen peptides produced by the methods described above 1. Platelet Aggregation Fresh whole blood was collected and mixed with 0.013 M sodium citrate and platelet-rich plasma was prepared according to the method of Meloni et al., *J. Biol. Chem.* 266, 6786 (1991). Platelet-rich plasma with a normalized platelet count between 2-2.5×10$^8$ platelets/ml was added to a cuvette of an aggregometer (Chronlog Corp., Havertown, Pa.), standardized using the protocol of Meloni et al., supra. Peptides to be examined were added to the cuvette and the mixture stabilized for a few moments. Once the baseline was stabilized, γ-thrombin (10-70 nM) (Haematologic Technologies, Essex Junction, Vt.) was added to determine the minimal concentration of the agonist necessary to achieve full platelet aggregation. All investigations with peptides were performed using threshold concentrations of γ-thrombin. Aggregation was allowed to proceed for 5 minutes before stopping.

Table III is a tabulation of the library of peptides prepared and their influence on γ-thrombin-induced platelet aggregation in platelet-rich plasma. Peptides are listed from the most potent to the least potent inhibitor of gamma thrombin-induced platelet aggregation. The numbers in the column represent the minimal concentration (mM) of the peptide that blocked 100% γ-thrombin-induced platelet aggregation of platelets in human platelet-rich plasma.

TABLE III

Effect of Peptides on Thrombin-Induced Platelet Aggregation

| Peptide | Concentration of Peptide [mM] That Gives 100% Inhibition | SEM |
|---|---|---|
| rOicPGF | 0.142 | 0.02 |
| rOicPaF(p-Me) | 0.016 | 0.004 |
| rOicPsF(p-Me) | 0.016 | 0.004 |
| rOicPaF(p-Br) | 0.018 | 0.004 |
| rOicPaF(p-I) | 0.023 | 0.003 |
| rOicPaF(p-NO$_2$) | 0.033 | 0.008 |
| PF(p-Me)Oicra | 0.150 | |

Human platelet samples were stimulated with 40 nM human gamma thrombin in each experiment.

As indicated in Table III, 40 nM γ-thrombin induced a full platelet aggregatory response. The aggregation response was abolished by greater than or equal to 16 μM rOicPaF(p-Me). At 8 μM rOicPaF(p-Me), γ-thrombin-induced platelet aggregation returned to normal. In Table III, 16 μM rOicPsF(p-Me), 18 μM rOicPaF(p-Br), 23 μM rOicPaF(p-I), and 33 μM rOicPaF(p-NO$_2$) also abolished 40 nM γ-thrombin-induced platelet aggregation. Peptide PF(p-Me)Oicra abolished 30 nM γ-thrombin-induced platelet aggregation at 150 μM.

2. Calcium Mobilization Assay

Figure 2:
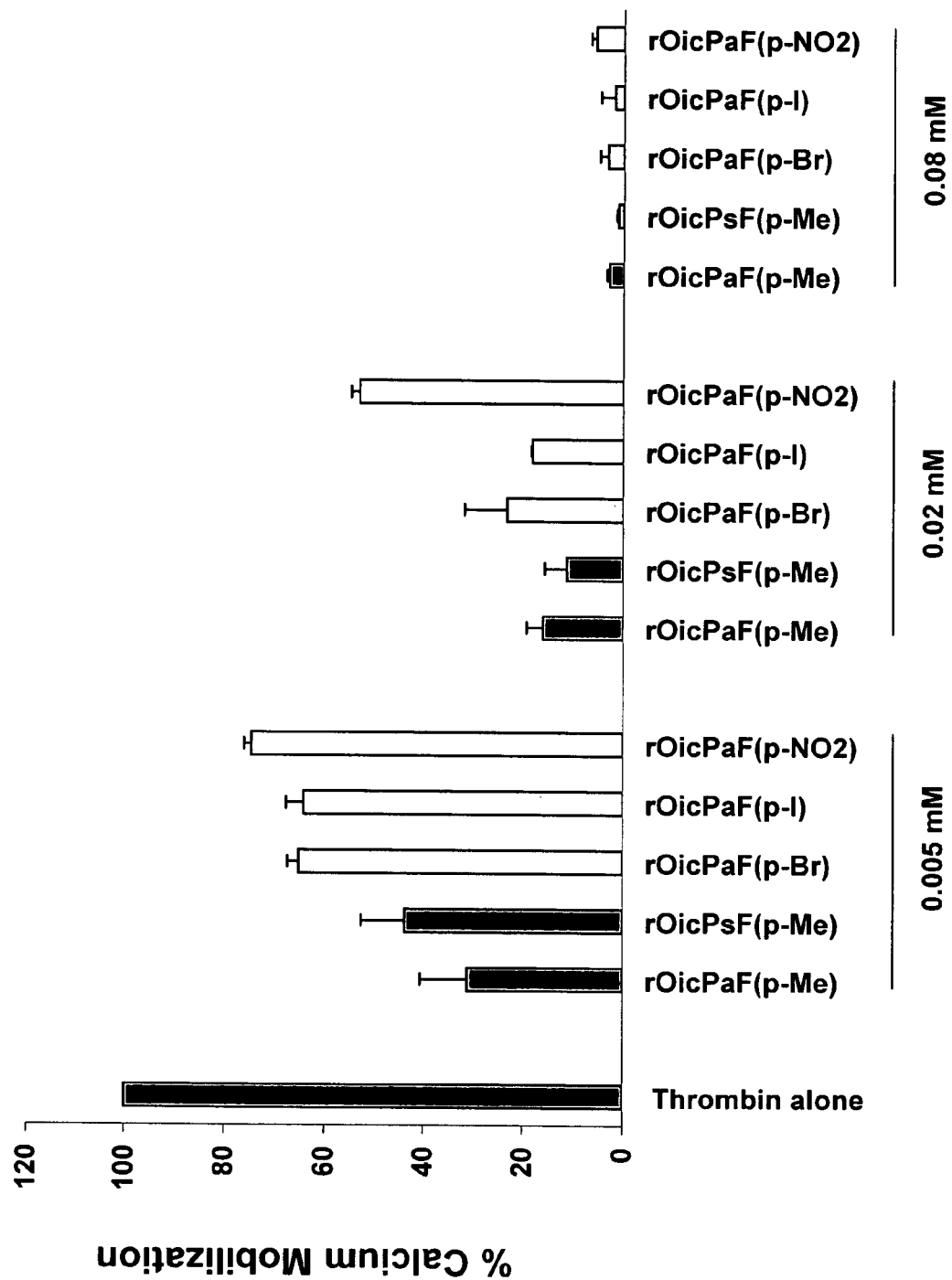
FIG. 2 illustrates the effect of rOicPaF(p-Br), rOicPaF(p-I), and rOicPaF(p-NO$_2$) on α-thrombin-induced calcium mobilization in normal human lung fibroblasts. The graph depicts a comparison to rOicPaF(p-Me) and rOicPsF(p-Me) with the above peptides at selected concentrations of 0.08 mM, 0.02 mM, and 0.005 mM, respectively. Two nM alpha thrombin was able to stimulate maximal calcium flux. At 0.08 mM of any of the above peptides, there was ≧95% inhibition of calcium mobilization. As the concentration of the peptides was decreased from 0.08 mM to 0.02 mM, there was decreased inhibition of thrombin-induced calcium mobilization to 84% for rOicPaF(p-Br), 88% rOicPaF(p-I), and 47% for rOicPaF(p-NO$_2$). At 0.005 mM peptides, there was only 35% inhibition for rOicPaF(p-Br), 36% inhibition for rOicPaF(p-I) and 26% inhibition for rOicPaF(p-NO2). In all cases rOicPaF(p-Me) or rOicPsF(p-Me) were more potent inhibitors.

The second assay developed to assess peptides from the combinatorial libraries uses inhibition of α-thrombin-induced calcium mobilization in fibroblasts. Normal human lung fibroblasts (NHLF) were purchased from Clonetics, San Diego, Calif., an affiliate of Bio-Wittaker, Walkersville, Md. The cytoplasmic free Ca$^{2+}$ concentration ([Ca$^{2+}$]$_i$) was measured using the fluorescent Ca$^{2+}$ indicator fura-2 (Molecular Probes, Inc., Eugene, Oreg.). Suspension of fibroblasts in Hepes-Tyrode's buffer were loaded with fura-2 by incubation at 37° C. with 2 μM fura-2/acetoxymethyl ester for 45 minutes according to the method of Rasmussen et al., *J. Biol. Chem.* 268, 14322 (1993). The labeled fibroblasts were separated from excess probe by washing by centrifugation at 1000 rpm (180 xg). Aliquots of the labeled fibroblasts were transferred into a quartz cuvette with a magnetic stirrer, which was then placed in a thermostatically controlled chamber at 37° C. in a fluorescence spectrophotometer (Perkin-Elmer LS50B spectrofluorometer, Chicago, Ill.). Reagents, test peptide, and α-thrombin (0.25-2 nM), were sequentially added directly to the cuvette. The excitation wavelengths varied between 340 and 380 nm. Fluorescence was measured by recording emitted light at 510 nm as reported by Fisher et al., *Mol Pharm.* 35, 195 (1989). The minimum emission was determined on a solubilized fibroblast sample in the presence of 10 mM EDTA; maximum emission was determined on the same sample with 10 mM $Ca^{2+}$ added. The intrafibroblast free $Ca^{2+}$ concentration was calculated by the method of Grykiewicz et al., *J. Biol. Chem.* 260, 3440 (1985). The ratio of the fluorescence readings was calculated as R=340/380 nm and processed according to the equation $[Ca^{2+}]_i = K_D((R-R_{min})/(R_{max}-R))(S_{f2}/S_{b2})$ to determine the intrafibroblast free $Ca^{2+}$ concentration. The $K_D$ for fura-2 was assumed to be 224 nM. $R_{max}$ and $R_{min}$ are the maximum and minimum fluorescence ratios measured at the end of the experiment, respectively; $S_{f2}$ and $S_{b2}$ are the fluorescence values at 380 nm in the absence and presence of saturating $[Ca^{2+}]$, respectively. The reaction was monitored for 3-5 minutes. As shown in FIG. 1, peptide rOicPaF(p-Me) (D-Arg-Oic-Pro-D-Ala-Phe(p-Me)) and peptide rOicPsF(p-Me) (D-Arg-Oic-Pro-D-Ser-Phe(p-Me)) completely blocked 1 nM α-thrombin-induced $Ca^{2+}$ mobilization in fibroblasts at concentrations ≧40 μM. As shown in FIG. 2, peptides rOicPaF(p-Br), rOicPaF(p-I), or rOicPaF(p-$NO_2$) completely blocked 1.0 nM α-thrombin-induced $Ca^{2+}$ mobilization in fibroblasts at concentrations between 20-80 μM.

3. Inhibition of Clot-based Coagulant Assays

Figure 3:
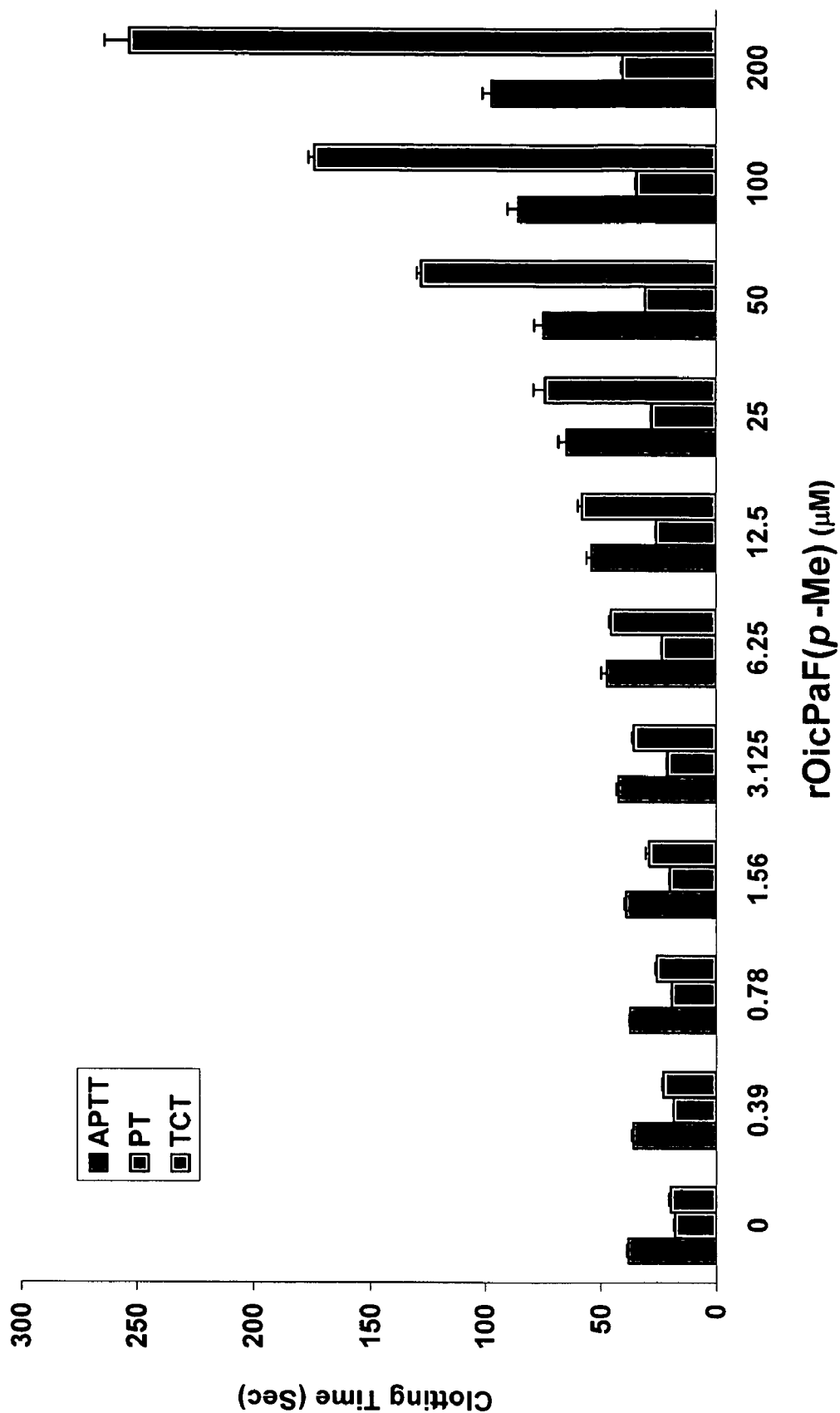
FIG. 3 illustrates the effect peptide rOicPaF(p-Me) has on the clotting time of normal human plasma using the activated partial thromboplastin time (APTT), prothrombin time (PT), or thrombin clotting time (TCT). At 1.56 μM, 1.56 μM, or 0.78 μM peptide rOicPaF(p-Me), there was a significant prolongation (p<0.05) of the APTT, PT, or TCT, respectively. These data indicate that peptide rOicPaF(p-Me) also has a significant effect of directly interacting with α-thrombin itself.
Figure 4:
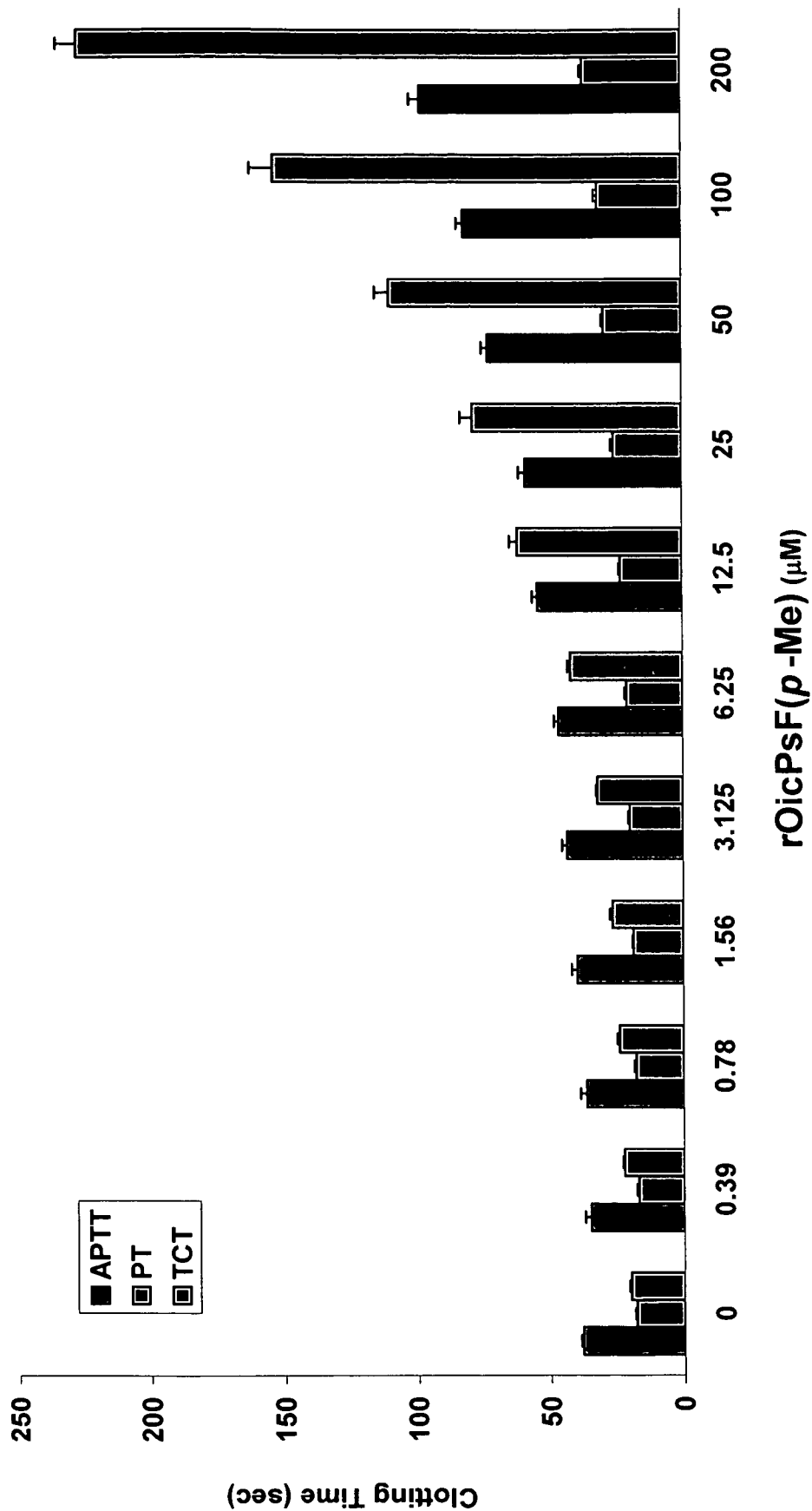
FIG. 4 illustrates the effect of peptide rOicPsF(p-Me) on the clotting time of normal human plasma using the activated partial thromboplastin time (APTT), prothrombin time (PT), or thrombin clotting time (TCT). At 3.13 μM, 1.56 μM, or 0.39 μM peptide rOicPsF(p-Me), there was a significant prolongation (p<0.05) of the APTT, PT, or TCT, respectively. These data indicate that peptide rOicPsF(p-Me) also has a significant effect of directly interacting with α-thrombin itself.
Figure 5:
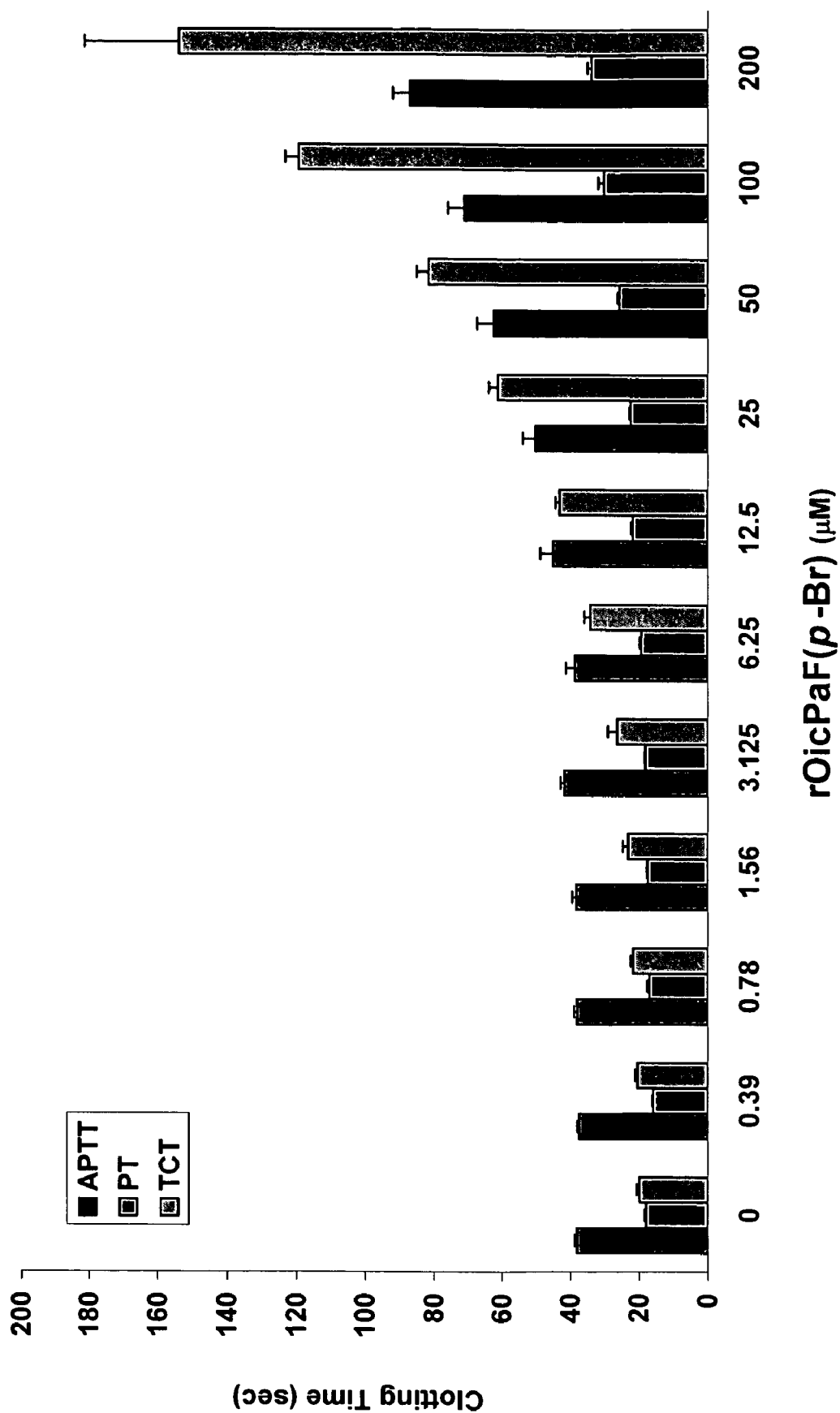
FIG. 5 illustrates the effect of peptide rOicPaF(p-Br) on the clotting time of normal human plasma using the activated partial thromboplastin time (APTT), prothrombin time (PT), or thrombin clotting time (TCT). At 12.5 μM, 6.25 μM, or 0.78 μM peptide rOicPaF(p-Br), there was a significant prolongation (p<0.05) of the APTT, PT, or TCT, respectively. These data indicate that peptide rOicPaF(p-Br) also has a significant effect of directly interacting with α-thrombin itself.
Figure 6:
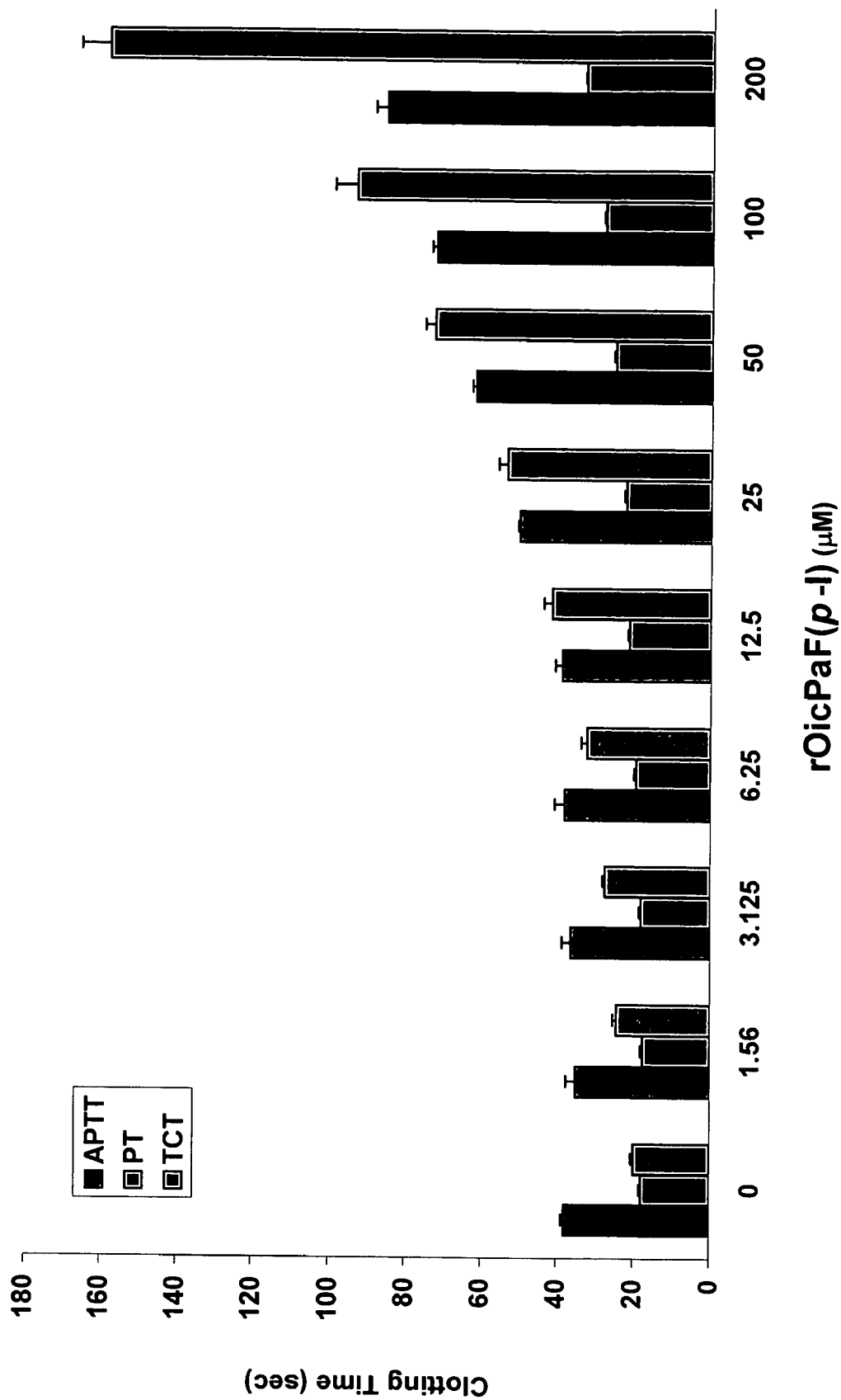
FIG. 6 illustrates the effect peptide rOicPaF(p-I) has on the clotting time of normal human plasma using the activated partial thromboplastin time (APTT), prothrombin time (PT), or thrombin clotting time (TCT). At 25 μM, 6.25 μM, or 0.78 μM peptide rOicPaF(p-I), there was a significant prolongation (p<0.05) of the APTT, PT, or TCT, respectively. These data indicate that peptide rOicPaF(p-I) has a significant effect of directly interacting with α-thrombin itself.
Figure 7:
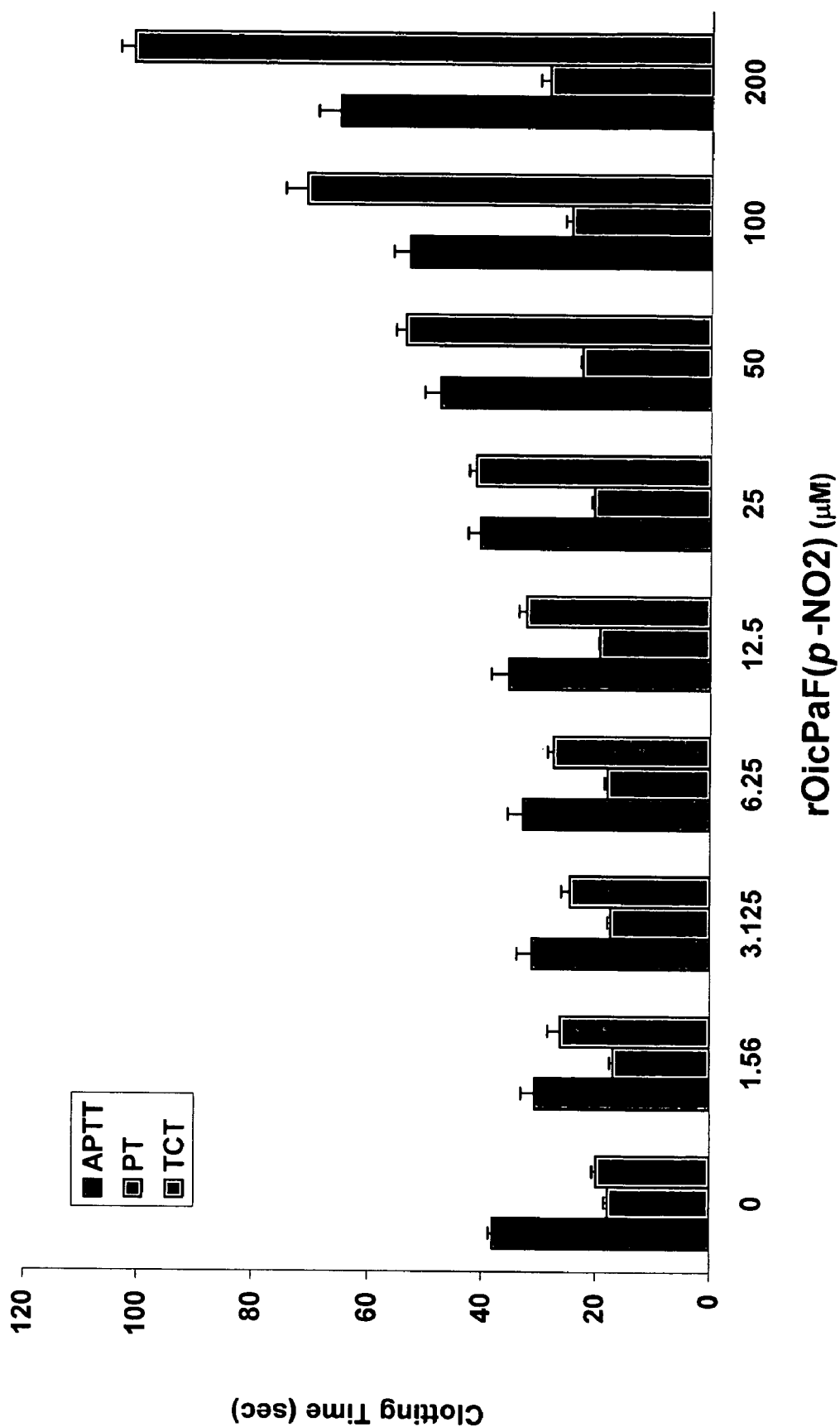
FIG. 7 illustrates the effect peptide rOicPaF(p-NO$_2$) has on the clotting time of normal human plasma using the activated partial thromboplastin time (APTT), prothrombin time (PT), or thrombin clotting time (TCT). At 50 μM, 6.25 μM, or 1.56 μM peptide rOicPaF(p-NO$_2$), there was a significant prolongation (p<0.05) of the APTT, PT, or TCT, respectively. These data indicate that peptide rOicPaF(p-NO$_2$) has a significant effect of directly interacting with α-thrombin itself.

The influence of the various peptide formulations used in the present invention on established coagulation-based assays was determined. The activated partial thromboplastin time (APTT) is performed by mixing 0.05 ml normal human citrated plasma with 0.05 ml activated partial thromboplastin reagent purchased from Organon Teknika, Research Triangle Park, NC in the absence or presence of a peptide inhibitor. After incubation for 5 min at 37° C., the mixture is recalcified with 0.05 ml of 30 mM calcium chloride and the time to clot formation is measured in an Amelung KC4A instrument (Sigma Chemical Corp, St. Louis, Mo.) (Hasan et al. *Thrombosis and Haemostasis.* 82, 1182-1187 (1999)). The prothrombin time (PT) is performed by mixing 0.05 ml normal human citrated plasma with 0.05 ml Simplastin (Organon Teknika, Research Triangle Park, NC) followed by incubation for 3 min at 37° C. in the absence or presence of a peptide inhibitor. At the addition of 0.05 ml of 30 mM calcium chloride, the time to clot formation is measured in an KC4A instrument (Sigma Chemical Corp, St. Louis, Mo.) (Hasan et al. *Thrombosis and Haemostasis.* 82, 1182-1187 (1999)). The thrombin clotting time (TCT) is performed by adding 0.1 ml normal human citrated plasma in the absence or presence of a peptide inhibitor and 0.05 ml of a α-thrombin solution such that the final concentration of the thrombin in the entire mixture was 1 nM. Upon addition of the thrombin, the time to clot formation is measured in an KC4A instrument (Sigma Chemical Corp, St. Louis, Mo.). In FIG. 3, peptide rOicPaF(p-Me) produces a significant prolongation (p<0.05) of the activated partial thromboplastin time at 1.56 μM, of the prothrombin time at 1.56 μM, and the thrombin clotting time at 0.78 μM, respectively. In FIG. 4, peptide rOicPsF(p-Me) produced a significant prolongation (p<0.05) of the activated partial thromboplastin time at 3.13 μM, of the prothrombin time at 1.56 μM, and the thrombin clotting time at 0.39 μM. In FIG. 5, peptide rOicPaF(p-Br) produced a significant prolongation (p<0.05) of the activated partial thromboplastin time at 12.5 μM, of the prothrombin time at 6.25 μM, and the thrombin clotting time at 0.78 μM. In FIG. 6, peptide rOicPaF(p-I) produced a significant prolongation (p<0.05) of the activated partial thromboplastin time at 25 μM, of the prothrombin time at 6.25 μM, and the thrombin clotting time at 0.78 μM. In FIG. 7, peptide rOicPsF(p-Me) produced a significant prolongation (p<0.05) of the activated partial thromboplastin time at 50 μM, of the prothrombin time at 6.25 μM, and the thrombin clotting time at 1.56 μM.

4. Inhibition of RPPGF (SEQ ID NO: 4)-biotin Binding to $rPAR1_{EC}$ by rOicPaF(p-Me) and rOicPGF A recombinant form of the extracellular domain of human PAR1 was prepared. A portion of the extracellular domain of human PAR1 ($Ala^{26}$-$Ser^{99}$) ($rPAR1_{EC}$) was expressed in *Escherichia coli* using Novagen's bacterial expression system and its pET31b vector. Oligonucleotides primers for PCR were designed to place Nde1 and Xho1 restriction sites at the 5' and 3' ends of the coding sequence, respectively. Polymerase chain reaction (PCR) using human PAR1 cDNA as template prepared hPAR1 DNA encoding residues $Ala^{26}$-$Ser^{99}$. The Nde1-Xho1 PCR fragment was ligated to the Nde1/Xho1 sites of pET31b to create pET31b/$PAR1_{EC}$. This plasmid was then used to transform NovaBlue, an *E. coli* K12 strain. The insert of the cloned DNA was sequenced and it showed 100% fidelity with the DNA sequence of the targeted N-terminal extracellular domain of PAR1. The $rPAR1_{EC}$ was produced in *E. coli* strain BL21(DE3) (Novagen, Inc., Madison, Wis.) by transforming with pET31b/$PAR1_{EC}$ and inducing it with 1 mM IPTG (isopropyl-β-D-thiogalactopyranoside) for 5 h according to the published procedure of Nieman et al., *FEBS Letters* 579,25 (2005)). The expressed $rPAR1_{EC}$ ($Ala^{26}$-$Ser^{99}$) fusion protein was purified from bacterial lysates by nickel-chelate affinity chromatography (His-Trap™ Affinity Column, Amersham Pharmacia Biotech, Inc., Piscataway, N.J.) followed by treatment with CNBr to remove the KSI fusion protein and the His tag according to the manufacturer's protocol (Novagen, Madison, Wis.). The final recombinant protein was further purified by HPLC. Recombinant $PAR1_{EC}$ was characterized by 16.5% tris-tricine sodium dodecyl sulfate polyacrylamide gel electrophoresis (SDS-PAGE), amino-terminal sequencing and immunoblotting with anti-PAR1 antibodies which consist of a polyclonal antibody in goats and a monoclonal antibody both raised to the peptide Asn-Ala-Thr-Leu-Asp-Pro-Arg-Ser-Phe-Leu-Leu-Arg (SEQ ID NO:3).

Figure 8:
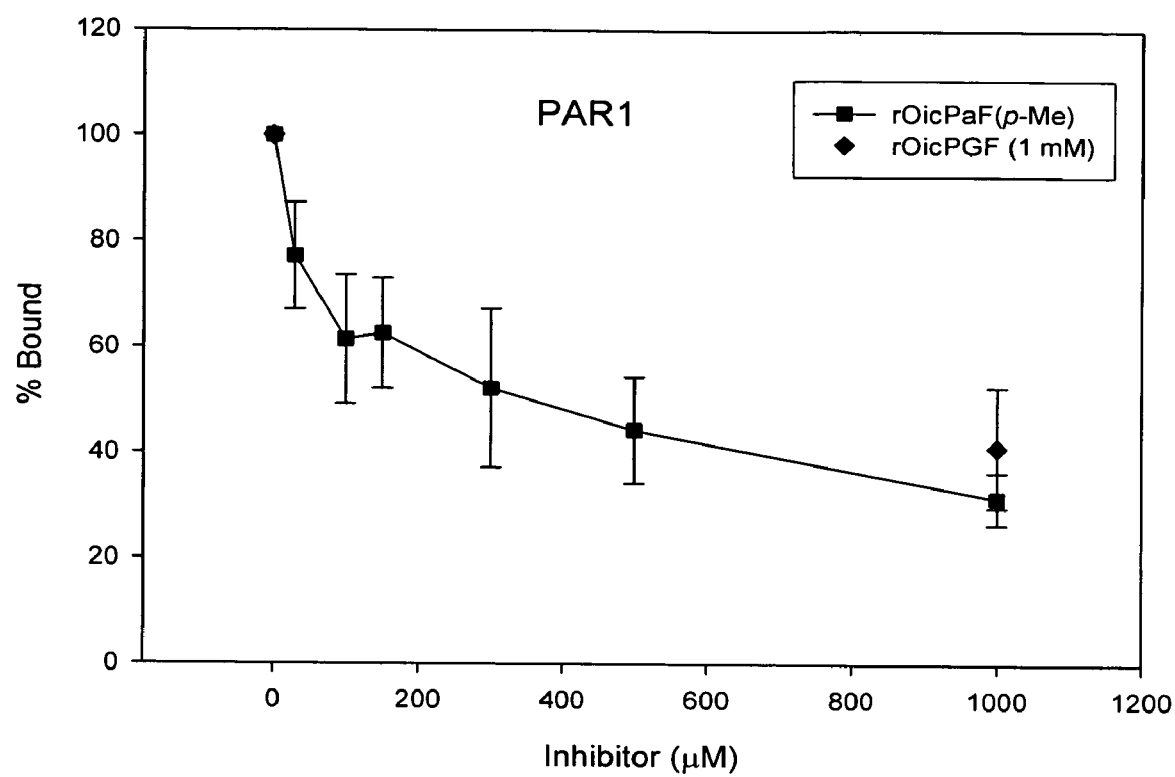
FIG. 8 illustrates the effect of rOicPaF(p-Me) on RPPGFK-biotin (SEQ ID NO: 15) binding to rPAR1 exodomain. The experiment measures whether the presence of various concentrations ranging from 30 μM to 1000 μM of rOicPaF(p-Me) interfered with binding of 15 μM RPPGFK-biotin (SEQ ID NO: 15) to the exodomain of PAR1. At 30 μM, 300 μM, and 1000 μM, rOicPaF(p-Me) displaced 23%, 52%, and 69% of RPPGFK-biotin (SEQ ID NO: 15), respectively. rOicPGF at 1 mM displaced 50% of RPPGFK-biotin (SEQ ID NO: 15) binding. The data indicates that rOicPaF(p-Me) binds to the exodomain of PAR1 even at low concentrations.

The interaction of RPPGFK-biotin (Arg-Pro-Pro-Gly-Phe-Lys-biotin, SEQ ID NO:15) with $rPAR1_{EC}$ is performed as follows: $rPAR1_{EC}$ is linked to microtiter plate cuvette wells at 1 μg/well on 0.1 M $Na_2CO_3$, pH 9.6 by overnight incubation at 4° C. After linking $rPAR1_{EC}$, 15 μM RPPGFK-biotin (SEQ ID NO:15) was incubated in the cuvette wells in the absence or presence of increasing concentration of various peptides, 30 to 1000 μM $rPAR1_{EC}$ rOicPaF(p-Me) or 1 mM rOicPGF. In FIG. 8, peptide rOicPaF(p-Me) blocked RPPGFK-biotin (SEQ ID NO:15) binding to $rPAR1_{EC}$ bound to the microtiter plate.

5. Inhibition of RPPGFK-biotin (SEQ ID NO: 15) Binding to $rPAR4_{EC}$ by rOicPaF(p-Me) and rOicPGF Investigations were performed to determine if the compounds in the present invention interact with the exodomain of human PAR4. The extracellular fragment of human PAR4 has been expressed in bacteria. Human erythroleukemia (HEL) cells were used as a source for PAR4 mRNA. The level of PAR4 mRNA was substantially higher in HEL cells than washed human platelets. The sense primer for PCR (5'-GAATTCCATATGGGCGGCACCCAGAC-CCCCAGCGTC-3', SEQ ID NO:16) had a Nde I restriction site and the antisense primer (5'-CCGCTCGAGTC-ACCTG-GTGGGCACCCAGCCCAGAAG-3', SEQ ID NO:17) has a Xho I site for cloning into the Novagen pET31b vector to prepare pET31b-PAR4 (Nieman et al., *FEBS Letters* 579, 25 (2005)). These primers give a 204 basepair fragment which codes for a 61 amino acid hPAR4 protein starting with $Gly^{18}$, the first amino acid after the signal peptide is removed, and finishing with $Arg^{78}$, the last amino acid of the extracellular fragment (Xu et al. *Proc. Natl. Acad. Sci.* 95, 6642-6646

Figure 9:
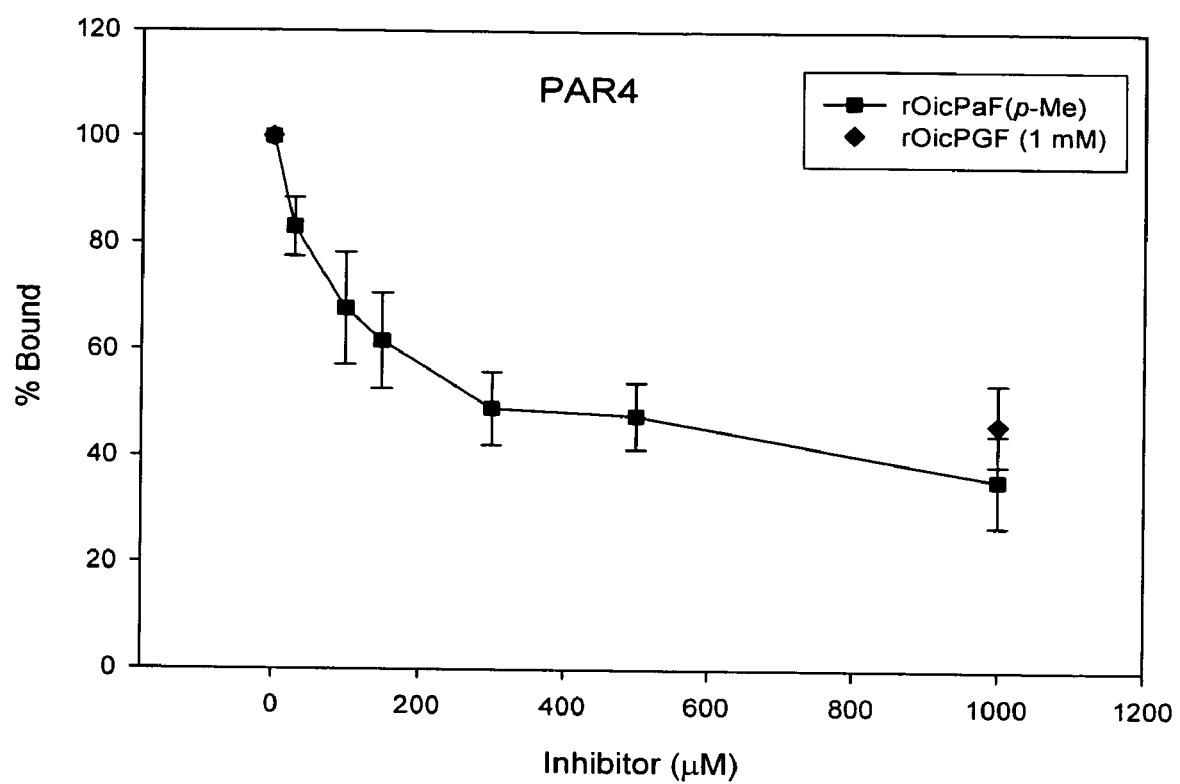
FIG. 9 illustrates the effect of rOicPaF(p-Me) on RPPGFK-biotin (SEQ ID NO: 15) binding to rPAR4 exodomain. The same experiment as described above was employed to measure whether the presence of various concentrations ranging from 30 μM to 1000 μM of rOicPaF(p-Me) interfered with binding of 15 μM RPPGFK-biotin (SEQ ID NO: 15) to the exodomain of PAR4. At 30 μM, 300 μM, and 1000 μM, rOicPaF(p-Me) displaced 19%, 49%, and 63% of RPPGFK-biotin (SEQ ID NO: 15), respectively. At 1 μM, rOicPGF displaced 50% of binding. The data indicate that rOicPaF(p-Me) binds to the exodomain of PAR4 even at low concentrations.

(1998)). The pET31b-PAR4 vector after cloning was used to transform BLD (DE3) cells to express the recombinant protein. After IPTG stimulation, the recombinant protein was isolated from the bacterial lysate on a nickel affinity column followed by treatment with CNBr to remove the KSI fusion protein and His-tag on its amino terminal end. The isolated recombinant extracellular domain of PAR4 (rPAR$_{EC}$) is about 9 kDa on 16.5% Tris-Tricine SDS-PAGE. The recombinant protein is recognized as being human PAR4 by detection with an antibody prepared from a peptide (S$^{41}$ILPAPRGYPGQ$^{52}$) (SEQ ID NO:9) from human PAR4$_{EC}$. Recombinant PAR4$_{EC}$ was linked to microtiter plate cuvette wells. Goat polyclonal antibody to human PAR1, PAR3, or PAR4 was incubated with the coated microtiter plate cuvette wells and antibody binding was detected. Only antibody to PAR4 detected rPAR4$_{EC}$ linked to the microtiter plate wells. In FIG. 9, investigations showed that 30-1000 µM rOicPaF(p-Me) or 1 mM rOicPGF block RPPGFK-biotin (SEQ ID NO:15) (15 µM) from binding to rPAR4$_{EC}$ that had been previous bound in 1 □g in 0.01 M Na$_2$CO$_3$, pH 9.6 to plastic microtiter plates. These studies indicate that peptides of the present invention also physically interact with human PAR4.

6. Inhibition of Alpha and Gamma Thrombin Hydrolysis of Chromogenic Substrates

Investigations were performed to determine if the present compounds inhibit the enzymatic activity of alpha and gamma thrombin. The ability of 20 nM rOicPaF(p-Me), rOicPsF(p-Me), rOicPaF(p-Br), rOicPaF(p-I), or 40 nM rOicPsF(p-NO$_2$) to inhibit the hydrolytic activity of human α-thrombin (1 nM) or γ-thrombin (1 nM) was measured in 10 mM Tris-HCl, 0.15 M NaCl, pH 7.6 containing 0.1% bovine serum albumin, using 0.6 mM Sar-Pro-Arg-paranitroanilide (Sigma) (K$_m$=138 µM) (Hasan et al., *Am J Physiol Heart Circ Physiol* 285, H183, (2003)). Additional studies determined the inhibition of 1 nM factor Xa (FXa) (Enzyme Research Laboratories) in 100 mM triethanolamine, 100 mM NaCl, pH 8.0, supplemented with 0.1% polyethyleneglycol (MW 8000) and 0.2% bovine serum albumin was determined using 0.4 mM N-(p-Tosyl)-Gly-Pro-Arg-paranitroanilide (Schmaier et al., *Biochemistry* 34, 1171 (1995)). Inhibition of 50 nM factor VIIa (FVIIa) (Haematologic Technologies) in a preformed complex with 70 nM soluble recombinant tissue factor, amino acids 1-219 (sTF$_{1-219}$), provided by Dr. Tom Girard, Monsanto, St. Louis, Mo. in 0.02 M Tris-HCl, 0.14 M NaCl, pH 7.4 containing 0.1% bovine serum albumin and 5 mM CaCl$_2$ was determined by hydrolysis of 1.25 mM methoxycarbonyl-D-cyclohexylglycyl-glycyl-arginine-p-nitroanilide (Spectrozyme fXa) (K$_m$=0.284 mM) (Mahdi et al. *Thromb Res* 99, 267 (2000)). Additional experiments were performed by incubation of the peptides with 50 nM FVIIa before the addition of 70 nM sTF$_{1-219}$. In these experiments, hydrolysis of the substrate was measured as described above. In all experiments, the initial rate of hydrolysis of the substrate in the absence or presence of the peptide inhibitor was obtained over 20 min by continuous monitoring the absorbance at 405 nm and taking a reading at 2 min intervals. Equilibrium inhibition constants were calculated by determining the K$_{i,app}$ and then the K$_i$ according to the procedure of Bieth (1984) as previously reported (Schmaier et al., *Biochemistry* 34, 1171 (1995)). As shown in Table IV, all peptides were inhibitors of alpha and gamma thrombin with K$_i$ between 6.6-10.6 and 54-88 µM, respectively. No peptide inhibited factor Xa or factor VIIa.

TABLE IV

Kinetic Inhibition Constants of Coagulation Enzymes

| | Enzyme | | | |
|---|---|---|---|---|
| Peptide | αIIa (2 nM)[‡] | γIIa (2 nM) | FXa (1 nM) | FVIIa-TF (50 nM)[£] |
| | K$_i$ (µM) + SD | | | |
| rOicPaF(p-Me) | 6.6 ± 0.8 | 54.3 ± 16 | — | — |
| rOicPsF(p-Me) | 6.7 ± 0.7 | 42.2 ± 6 | — | — |
| rOicPaF(p-Br) | 7.3 ± 2 | 48.7 ± 7 | — | — |
| rOicPsF(p-I) | 6.4 ± 1 | 59.2 ± 13 | — | — |
| rOicPsF(p-NO2) | 10.6 ± 2 | 87.9 ± 16 | — | — |

[‡]The numbers in parenthesis are the concentrations of the enzyme used in the reaction.
[£]The concentration of tissue factor used in the experiment was 70 nM.

Table IV illustrates the effect of the peptides rOicPaF(p-Me) (D-Arg-Oic-Pro-D-Ala-Phe(p-Me)), rOicPsF(p-Me) (D-Arg-Oic-Pro-D-Ser-Phe(p-Me)), rOicPaF(p-Br) (D-Arg-Oic-Pro-D-Ala-Phe(p-Br)), rOicPaF(p-I) (D-Arg-Oic-Pro-D-Ala-Phe(p-I)), and rOicPaF(p-NO$_2$) (D-Arg-Oic-Pro-D-Ala-Phe(p-NO$_2$)) on the enzymatic activity of alpha-thrombin (2 nM), gamma-thrombin (2 nM), factor Xa (FXa at 1 nM), and factor VIIa without pre-incubation with tissue factor (FVIIa-TF at 50 nM) or with pre-incubation with tissue factor (FVIIa-TF preformed). rOicPaF(p-Me), rOicPsF(p-Me), rOicPaF(p-Br), rOicPaF(p-I), and rOicPs(p-NO2) inhibited the enzymatic activity of both alpha-thrombin and gamma-thrombin with a K$_i$ value ranging from 6.4-10.6 µM and 42-87.9 µM, respectively. The above peptides did not inhibit the enzymatic activity of clotting FXa or FVIIa.

Table V indicates the peptide sequence and peptide mass (M+H) determined for each sequence by analysis with LC/MS/MS

TABLE V

Designations, Sequence and Mass (M + H) for Peptide Analogs.

| Peptide Sequence | M + H |
|---|---|
| H-r-Oic-P-G-Thi-NH2 | 632.2 |
| H-r-Oic-PG-Idg-NH2 | 652.4 |
| H-r-Oic-Hyp-G-Thi-NH2 | 648.4 |
| H-r-Oic-Hyp-G-Idg-NH2 | 668.4 |
| H-r-Oic-Oic-G-Thi-NH2 | 686.3 |
| H-r-Oic-Oic-G-Idg-NH2 | 705.8 |
| H-r-Oic-PGF-NH2 | 626.3 |
| H-r-Oic-P-a-F-NH2 | 639.6 |
| H-r-Oic-P-a-F(p-Me)-NH2 | 654.4 |
| H-R-P-P | 369.3 |
| H-r-Oic-P | 422.5 |

(The initial "H" on each peptide in Table V indicates that the N-terminus was unmodified.)

7. Inhibition of Thrombosis in the Mouse

Figure 10:
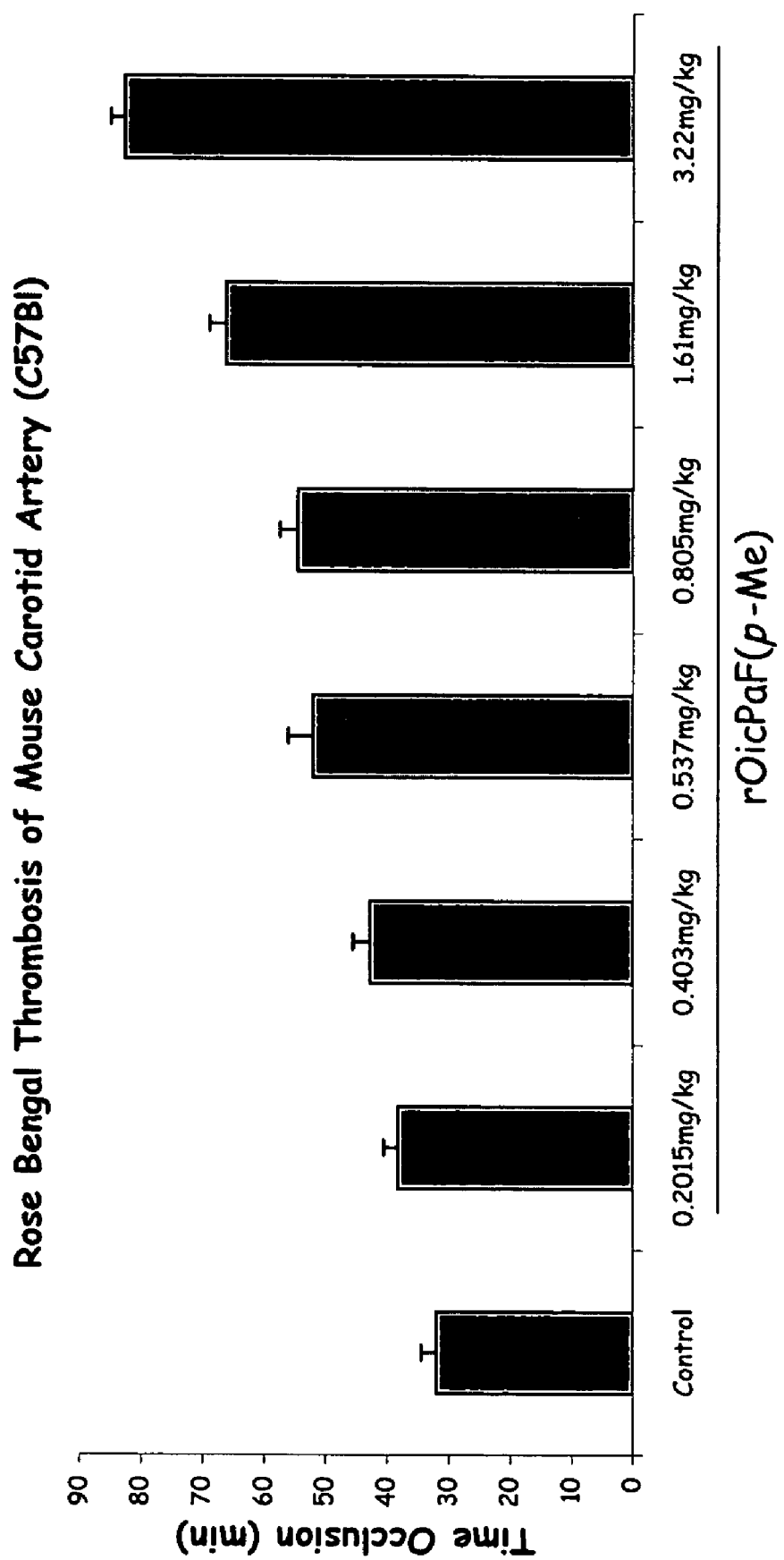
FIG. 10 shows that rOicPaF(p-Me) prevents thrombosis in the mouse. Increasing concentrations of rOicPaF(p-Me) from 0.2 to 3.22 mg/kg IP produces a significant prolongation in the time to occlusion of the mouse right carotid artery in the Rose Bengal model for arterial thrombosis.
Figure 11:
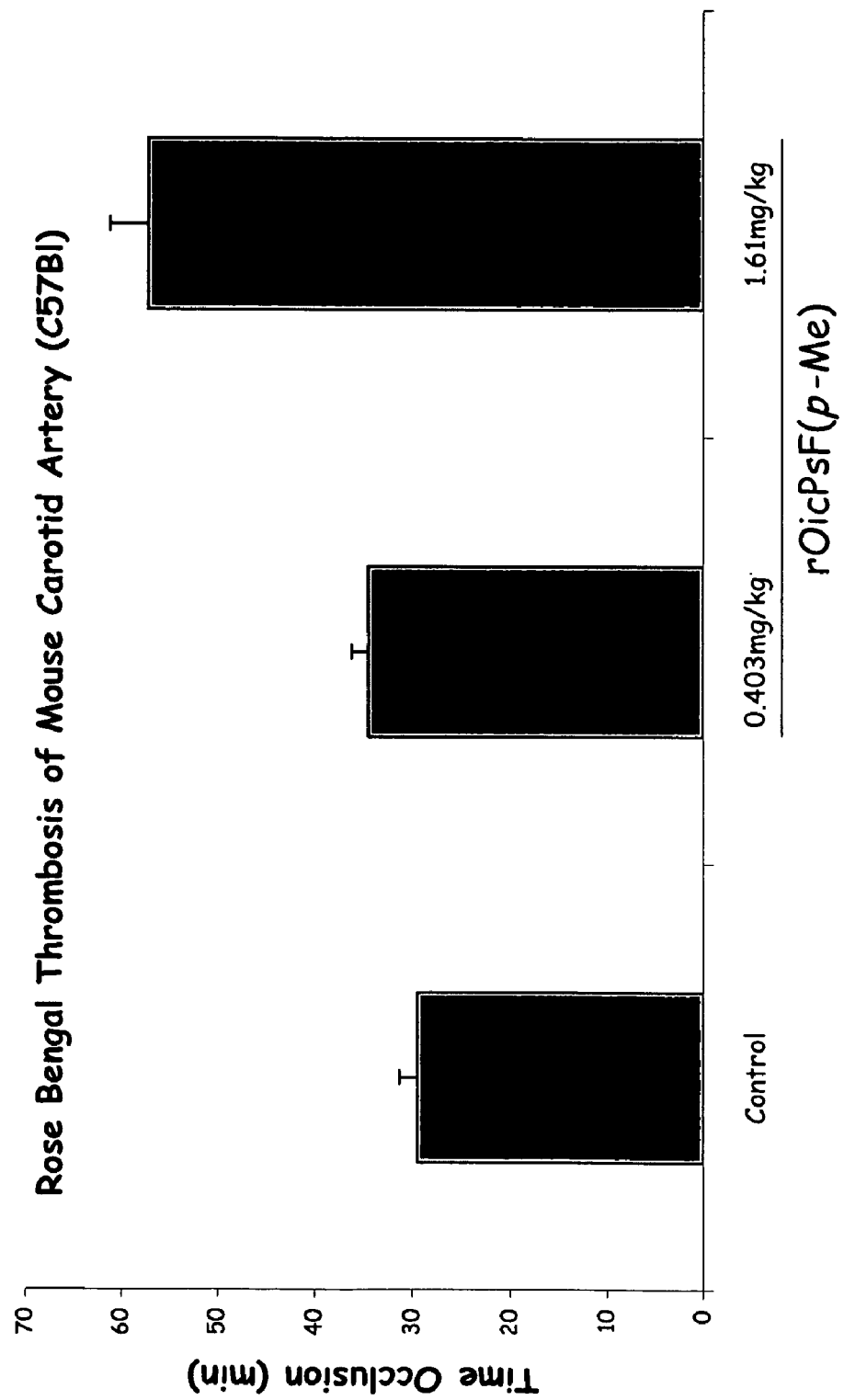
FIG. 11 shows that rOicPsF(p-Me) prevents thrombosis in the mouse. Increasing concentrations of rOicPsF(p-Me) from 0.4 to 1.61 mg/kg IP produces a significant prolongation in the time to occlusion of the mouse right carotid artery on the Rose Bengal model for arterial thrombosis.

Investigations were performed to demonstrate if the compounds rOicPaF(p-Me) or rOicPsF(p-Me) inhibit arterial thrombosis in the mouse. C57BL6 mice 6 to 16 weeks of age were anesthetized by intraperitoneal injection with sodium pentobarbital and placed in the supine position on a dissecting microscope (Nikon SMZ-2T, Mager Scientific, Inc., Dexter, Mich.). A midline surgical incision was made to expose the right common carotid artery and a Doppler flow probe (Model 0.5 VB, Transonic Systems, Ithaca, N.Y.) is placed under the vessel. The probe was connected to a flowmeter (Transonic Model T106) and was interpreted with a computerized data acquisition program (Windaq, DATAQ Instruments, Arkron, Ohio). Rose Bengal (4,5,6,7-tetrachloro-3',6-dihydroxy-2,4, 5,7-tetraiodospiro(isobenzofuran-1(3H), 9 [9H] xanthan)-3-1 dipotassium salt) (Fisher Scientific, Fair Lawn, N.J.) at 50 mg/kg in 0.9% saline) was then injected into the tail vein in a 0.12 ml volume (Eitzman et al., *Blood* 95, 577 (2000)). After injection into the tail vein, a green laser light (Melles Griot, Carlsbad, Calif.) at a wavelength of 540 nm was applied 6 cm from the carotid artery. Flow is monitored continuously from the onset of injury. The time to occlusion was determined only after the vessel remained closed with a cessation of blood flow for 20 min. As shown in FIG. 10, rOicPaF(p-Me) in a concentration-dependent manner from 0.2 to 3.2 mg/kg after intraperitoneal injection progressively prolonged the time to carotid artery occlusion in C57BL6 mice. Similarly, rOicPsF (p-Me) beginning at 0.4 mg/kg after intraperitoneal injection also prolonged the time to carotid artery occlusion in the mouse as shown in FIG. 11. These investigations indicate that these compounds are able to prevent thrombosis in the whole animal in vivo.

8. Stability Testing in Buffer, Intestinal Perfusate, and Intestinal Homogenate of Peptides Stability testing of the various compounds was performed in buffer, intestinal perfusate, and an intestinal homogenate preparation to assess the potential oral availability of these compounds. Initial studies prepared the tissue for stability studies. The buffer used in stability testing is 10 mM MES (pH 6.5) containing 135 mM NaCl, and 5 mM KCl. To collect intestinal perfusate from rats, male Sprague Dawley rats, 8 to 10 weeks old, weighing 250 to 350 g were fasted 15 to 18 hours with water given ad libitum. Anesthesia was administered by intramuscular injection of pentobarbital/ketamine (40 mg/kg and 80 mg/kg, respectively). The rats were placed on a warming pad under a surgical lamp to maintain body temperature and jejunal intestinal segments were exposed through a midline, abdominal incision. Approximately 20 cm segment of the jejunum (2 to 4 cm distal to the ligament of Treitz) was cannulated and the intestinal segments were perfused with 10 mM MES (pH 6.5) containing 135 mM NaCl, and 5 mM KCl at a flow-rate of 0.5 ml/min at 37° C. using a constant infusion pump (Harvard Apparatus, South Natick, Mass.). The collected perfusate was stored at −80° C. until use for ex vivo stability studies. After collection, the perfused intestinal segments were flushed with ice-cold 0.15 M KCl solution and the animal was euthanized and the jejunal intestinal segment detached. The inner intestinal tissue layers are scraped out and homogenized in MES buffer (pH 6.5) in a ratio of 1 part of intestinal tissue to 5 parts buffer. Total protein content of the perfusate and the homogenate were determined using a Biorad protein assay kit. The intestinal homogenate samples were used immediately or rapidly frozen at −80° C. until stability analysis.

The actual stability testing protocol is as follows: A 0.1 ml aliquot of the synthetic peptide solution (1 mg/ml) was added to 0.9 ml of MES buffer, pH 6.5, intestinal perfusate, or intestinal homogenate at 37° C. Samples were mixed by vortexing and 100 microliter aliquots were removed over a 60 to 90 minute period for analysis of breakdown products. The 100 microliter sample aliquots were diluted 10 fold with water and subjected to solid phase extraction using a Waters Oasis HLB column. Briefly, the columns were preconditioned by passing 1 ml of MeOH and 1 ml of water over the column, and 1 ml of sample was added to the column. The column was washed with 5% methanol:95% water solution to remove proteins and salts, then eluted with 1 ml of 100% methanol. The methanol was removed by vacuum, and the sample was reconstituted in mobile phase for LC/MS/MS analysis.

LC/MS/MS analysis was performed on a HP1100 HPLC (Hewlett Packard) interfaced with a Quattro II MS/MS detector (Waters/Micromass). For the HPLC separation, a 10 µL aliquot of sample in a mobile phase consisting of an equal volume mixture of acetonitrile/water containing 0.5% formic acid was injected onto a 150 mm×2.2 mm, 5 µm C8 column (Higgins Analytical Inc) and developed at a flow rate of 0.2 ml/min for 5 minutes. The MS detector was used in single ion recording mode at a cone voltage of 50 Volts. The assignments for m/z for the thrombostatin analogs are given in Table VI.

Table VI indicates the half lives of the various compounds in MES buffer (pH 6.5), intestinal homogenate, and intestinal perfusate. rOicPaF(p-Me) appears to be the most stable compound overall in all the vehicles.

TABLE VI

The Half Lives of the Peptides in Various Mediums

| Compound | $t_{1/2}$ (min) MES Buffer (pH 6.5) | $t_{1/2}$ (min) Intestinal Perfusate | $t_{1/2}$ (min) Intestinal Homogenate |
| --- | --- | --- | --- |
| rOicPGThi | stable | nd | 32.40 |
| rOicHypGThi | 551.94 | 32.20 | 43.80 |
| rOicOicGThi | 129.68 | nd | nd |
| rOicPGF | 178.70 | 110.55 | 40.32 |
| rOicPaF | 604.13 | stable | stable |
| rOicPaF(p-Me) | 363.01 | 313.99 | 756.95 |
| rOicP | stable | stable | 934.62 |
| RPP | nd | 91.84 | nd |
| rOicPGIdg | nd | 56.14 | nd |
| rOicHypGIdg | nd | 204.85 | nd |

"nd" Not done

Figure 12:
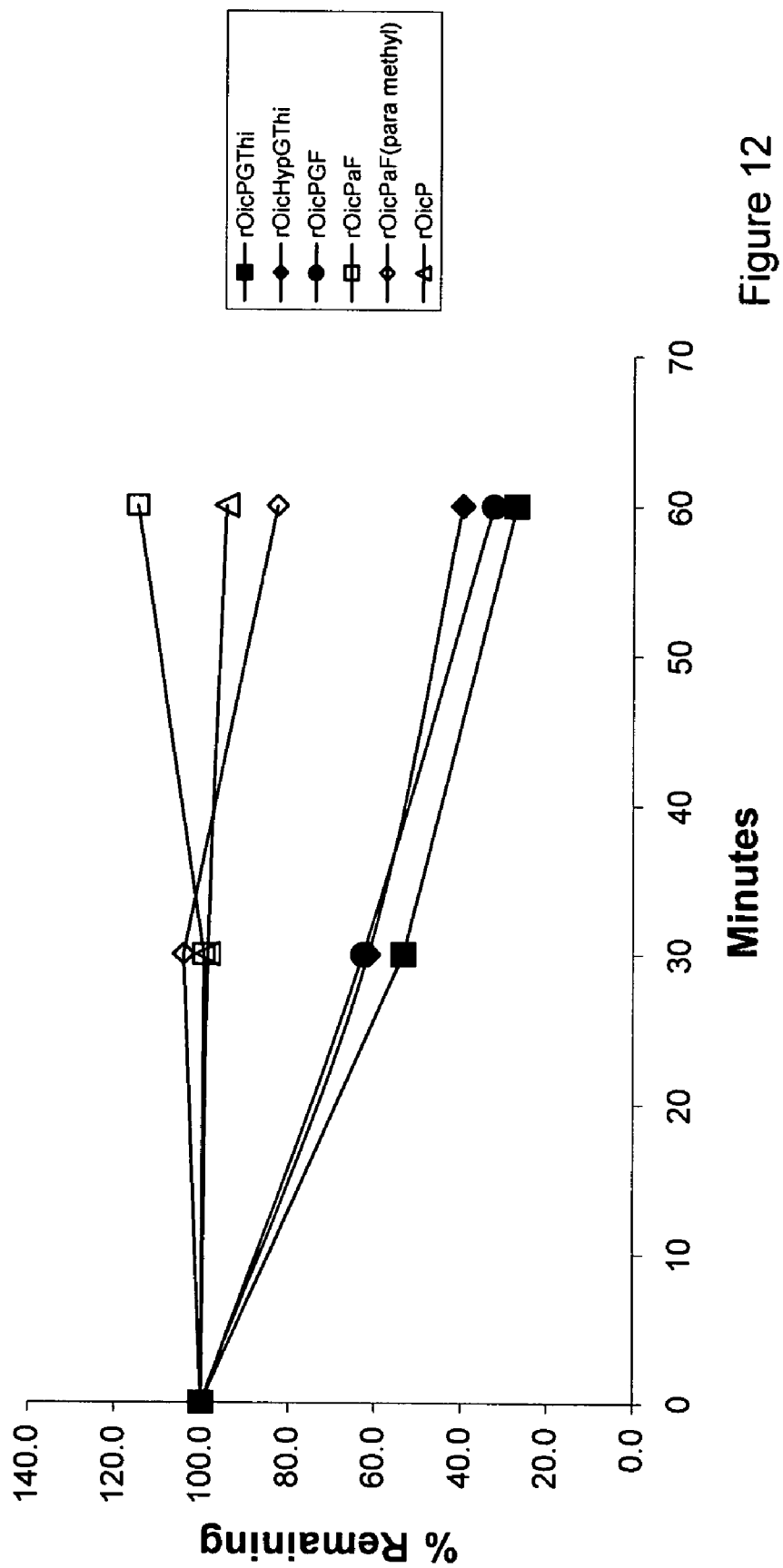
FIG. 12 shows various peptides' stability in intestinal homogenate. Peptides rOicP, rOicPaF(p-Me) and rOicPaF are the most stable. Peptides rOicHypGThi, rOicPGF, and rOicPGThi are less stable.

In order to determine the compounds with the highest potential for oral delivery, a series of stability tests were performed in media that approximated the intestinal environment. These included intestinal perfusate, which is comprised of buffered solution passed through an intestinal segment, and intestinal homogenate. In simple MES buffer, at pH 6.5, the half life of the compounds in pH 6.5 buffer varied from approximately 2 hours to stable over the time frame tested. As shown in Table VI the most to least stable compounds in MES buffer are: rOicPGThi>rOicP>rOicPaF>rOicHypGThi>rOicPaF(p-Me)>rOicPGF>rOicOicGThi. Compounds RPP, rOicPGIdg, and rOicHypGIdg were not tested for buffer stability. However, as seen in Table VI, in intestinal perfusates, the most to least stable compounds are rOicPaF, rOicP>rOicPaF(p-Me)>rOicHypGIdg>rOicPGF>RPP>rOicPGIdg, rOic-HypGThi. Further, in intestinal homogenates, the most to least stable compounds are rOicPaF, rOicP, rOicPaF(p-Me)> all others (Table VI, FIG. 12). From these data, it is clear that those compounds with few or no "natural" peptide bonds, e.g., rOicPaF(p-Me), rOicPaF, or rOicP are the most stable in the intestinal setting and are therefore more likely to be absorbed intact from the intestinal segment.

9. Permeability Determinations of Peptide Analogs

These same series of peptide analogs that included the most stable compounds determined in intestinal perfusate and homogenates were examined for intestinal permeability using rat intestinal in situ perfusion methodology (Friedman, D I and Amidon, G L, Pharm Res. 8(1), pp 93-96, 1991). To determine the intestinal permeability of the various peptide analogs, male albino Sprague-Dawley rats, 9-10 weeks old and weighing 250-350 g were fasted for 18 hours with free access to water. The rats were anesthetized with an intramuscular injection of ketamine/xylazine/butorphanol (87 mg/kg, 6 mg/kg, and 0.2 mg/kg body weight, respectively). The abdomen was opened by a 4-5 cm midline incision and a 10 cm jejunal segment was cannulated on two ends and connected to a syringe pump that pumps the perfusing solution through the cannulated intestine at a constant rate and at a temperature of 37° C. The isolated segment was rinsed with 10 mM MES (pH 6.5) at a flow-rate of 0.5 ml/min in order to clean out any residual debris. Jejunal perfusion was subsequently performed with the same buffer containing 135 mM NaCl, 5 mM KCl and 0.01% PEG 4000 at a flow rate of 0.2 ml/min containing test compound, internal permeability reference standards (e.g., metoprolol) and $^{14}$C-PEG 4000 as a non-absorbable marker for measuring water flux. After steady-state is reached within the perfused intestinal segment, typically 30 minutes after start of perfusion, samples were taken at 10 minute intervals for 1 hour. $^{14}$C (PEG-4000) levels are assayed by scintillation counting and test compounds and internal permeability standard analysis by LC/MS/MS. Samples are frozen and stored at −80° C. until analysis.

The effective permeability ($P_{eff}$) determined from the in situ perfusion [1] is calculated from equation 1

$$P_{eff}(\text{cm/sec}) = \frac{-Q\ln(C'_{out}/C'_{in})}{2\pi RL} \quad (1)$$

where Q is the perfusion buffer flow rate, $C'_{out}$ is the outlet concentration of the compound that has been adjusted for water transport (equation 2) after passing through the intestinal segment, $C'_{in}$ is the inlet or starting concentration of the compound, R is the radius of the intestinal segment (set to 0.2 cm) and L is the length of the intestinal segment. To correct for water transport, a non-absorbed radioactive tracer, $^{14}$C PEG-4000, is included in the perfusion buffer. The $C_{out}/C_{in}$ ratio is corrected for water transport according to equation 2:

$$\frac{C'_{out}}{C'_{in}} = \frac{C_{out}}{C_{in}} \times \frac{A_{in} - A_0}{A_{out} - A_0} \quad (2)$$

where $A_{out}-A_0$ is equal to the radioactivity counts in the outlet sample minus background (dpm) and $A_{in}-A_0$ is equal to the radioactivity counts in the inlet sample minus background (dpm).

In certain instances, in addition to perfusing the intestinal segment as described, plasma is drawn through a portal vein cannula to determine the amount of material entering the portal system during the perfusion. This additional experimental step can aid in determining the true intestinal permeability of unstable compounds. After steady state conditions are reached as described above, 0.5 ml aliquots of plasma are withdrawn from the portal vein at regular intervals throughout the experimental time frame. The plasma samples are deproteinated with acetonitrile and the sample is subjected to SPE and LC/MS analysis as described above. From the plasma concentration of compound, the mesenteric permeability can be determined by substitution into equation 3:

$$\text{Flux} = A * P_{e\text{-}mes} * C_i \quad 3)$$

where Flux is equal to the portal blood flow (estimated at 1 ml/min in the rat)×the steady state mesenteric blood concentration of the peptide analogs, A is the absorptive area of the intestine (estimated at 12.56 cm$^2$ in the rat intestine), $P_{e\text{-}mes}$ is the mesenteric Permeability (cm/sec), and $C_i$ is the starting concentration of drug in the perfusate (ug/ml).

Table VII indicates the permeability of various peptide analogs as measured by the in situ perfusion technique. As seen in Table VII, the stable peptide analogs, rOicPaF, rOicPaF(p-Me), and rOicP, showed modest intestinal permeability when measured by either the in situ methodology or by directly measuring the material in the mesenteric plasma during the perfusion. Even rOicPGF, which was relatively unstable in intestinal perfusate with a $t_{1/2}$ of 2 hours, showed measurable intestinal permeability when monitoring plasma levels of compound. The more stable peptide analogs, therefore, have good potential for oral delivery.

TABLE VII

Permeability of Peptides as measured by the In Situ Perfusion Technique

| Compound | Permeability (in situ) (cm/sec) | Permeability (mesenteric) (cm/sec) | Steady state mesenteric levels of compounds (ug/ml) |
|---|---|---|---|
| rOicPGF | Degraded | 4.51E−07 | 0.136 |
| rOiePaF | 6.20E−06 | 1.39E07 | 0.042 |
| rOicPaF(pMe) | 1.00E−06 | 3.09E−07 | 0.093 |
| rOicP | 7.60E−06 | 1.63E−06 | 0.491 |

B. Clinical Indications for the Present Invention

The compositions and methods of the present invention can be used, inter alia, in individuals where thrombin, PAR1, and/or PAR4 activation contribute to the disease processes. They will be particularly applicable to individuals with acute coronary syndromes (crescendo angina, myocardial infarction) and in individuals who have acute coronary syndromes and receive percutaneous transluminal coronary angioplasty (PTCA) with an artificial stent placement. The compositions of the present invention can be used as single agents (alone) or in combination(s) with other agents. These additional agents may include any one or number of the following drugs (including all of them): standard heparin, low molecular weight heparin, aspirin, ticlopidine, clopidogrel, abciximab, tirofiban, or eptifibatide. The compounds of the present invention may be administered intravenously or orally with the other agent(s) to treat individuals for acute coronary syndromes and during the related management. The compositions and methods of the invention should also be useful in the management of individuals with dacron grafts from peripheral bypass surgery and individuals with stents for carotid or renal artery stenosis. Agents such as those described herein may be useful in the management of patients with transient ischemic attacks, stroke in progression, and complete stroke in the brain.

Compounds and compositions of the invention may be administered under circumstances where inhibition of thrombin-induced platelet activation or platelet aggregation is sought. The compounds are for use and administration to subjects experiencing platelet thrombosis from any cause, and may be used prophylactically in surgery or catheterization for insertion of artificial dacron grafts and stents to prevent reocclusion events due to platelet thrombi. Thus, the compounds may be infused into individuals to prevent strokes and cerebral edema. The biologic targets of this invention, thrombin, human PAR1 and PAR4, may also be expressed on cells other than platelets and vascular endothelial cells. They are known, for example, to be expressed on cancer cells (Chay et al. *Urology* 60, 760-765 (2002), Hu et al. *Blood* 104, 2764 (2004)). Thus, the compounds of the present invention should be useful to prevent thrombin, PAR1 or PAR4 activation in cancer cells involved in tumor implantation, seeding, and metastasis (Liang et al., Blood 104, 2746-2751 (2004)). Further, the compounds of the present invention may be useful to interfere with other thrombin and/or PAR1- or PAR4-mediated activity. The compounds could be used to decrease thrombin-mediated brain edema (Jiang et al. *J Cerebral Blood Flow & Metabolism.* 22, 404-410 (2002)) and inflammation as seen after radiation therapy (Wang et al., *J Thromb Haemost.* 2, 2027 (2004) or inflammatory bowel disease (Vergnolle et al., *J Clin Invest.* 114, 1444, (2004)).

The compounds and compositions may be administered by any convenient means that will result in substantial delivery into the bloodstream, including intravenous or intranasal administration, dermal patch, rectal suppositories, or by oral administration. Intravenous administration is presently contemplated as the preferred administration route, although intranasal administration may also be utilized. Furthermore, the nature of the compounds in the present invention is such that they contain D and synthetic amino acids which are less biodegradable than peptides consisting of L amino acids. There is no natural peptide bond in these compounds. Therefore, oral delivery mechanisms are feasible for these compounds as well.

The compounds may be combined with any pharmaceutical carrier that is physiologically acceptable to the host. The pharmaceutical composition may be compounded according to conventional pharmaceutical techniques that will be familiar to persons of skill in the art. Physiologically acceptable carriers, excipients and stabilizers are described, for example in Remington's Pharmaceutical Sciences, 20$^{th}$ Ed. Mack Publishing Co. (2000). The carrier may be provided in a variety of forms depending on the form of preparation desired for administration. For parenteral administration, the carrier can comprise sterile water, and optionally other ingredients to aid solubility or preservative purposes. In intravenous administration, the compounds may be dissolved in appropriate intravenous delivery vehicles containing physiologically compatible substances, such as sterile sodium chloride having a buffered pH compatible with physiologic conditions, e.g. saline. Injectable suspension may also be prepared, in which case appropriate liquid carriers, suspending agents and the like may be employed.

For oral delivery, the excipient formulation may contain inert customary ingredients or carriers such as sodium citrate or dicalcium phosphate and (a) binders, as for example, carboxymethylcellulose, alignates, gelatin, polyvinylpyrrolidone, sucrose, and acacia, (b) humectants, as for example, glycerol, (c) disintegrating agents, as for example, agar-agar, calcium carbonate, potato or tapioca starch, alginic acid, certain complex silicates, and sodium carbonate, (d) wetting agents, as for example, cetyl alcohol, and glycerol monostearate, (e) adsorbents, as for example, kaolin and bentonite, (f) fillers, such as lactose, starches, saccharides, sucrose, glucose, mannitol, and silicic acid, and (g) lubricants, as for example, magnesium stearate, talc, calcium stearate, solid polyethylene glycols, sodium lauryl sulfate, or mixtures thereof. These and other suitable pharmaceutically acceptable excipients are described in Remington's Pharmaceutical Sciences and in Handbook of Pharmaceutical Excipients, 3$^{rd}$ edition, Ed. Arthur H. Kibbe (American Pharmaceutical Association, Washington, D.C. 1999)

The dosage of administration will depend on the size and weight of the patient. Those skilled in the art of infusion therapy in ICU or in interventional cardiology can derive appropriate dosages and schedules of administration to suit the specific circumstances and needs of the patient. The physiologically acceptable dosages generally range from about 1 to 10 mg per day per kg of body weight. In preferred intravenous administration, the dosage is 1 mg/kg body weight in 5 ml of normal saline or in any suitable vehicle given at a rate of 1 ml/min. The therapeutically optimal amounts of dosage may be determined by monitoring pre- and post-infusion platelet function by determining ex vivo γ-thrombin induced platelet aggregation and secretion, and also by measuring hemostatic parameters like activated partial thromboplastin time (APTT), prothrombin time (PT), thrombin clotting time (TCT), and template bleeding time (BT).

Publications cited herein are hereby incorporated by reference.

While the invention has been described in detail, and with reference to specific embodiments thereof, it will be apparent to one of ordinary skill in the art that various changes and modifications can be made therein without departing from the spirit and scope thereof.

We claim:

1. A compound comprising an amino acid sequence of formula $$A_1\text{-}A_2\text{-}A_3\text{-}A_4\text{-}A_5$$

Wherein
- $A_1$ is selected from the group consisting of D-arginine (r) and L-arginine (R);
- $A_2$ is selected from the group consisting of (2S, 3aS, 7aS)-octahydroindole-2-carboxlic acid (Oic) and P;
- $A_3$ is selected from the group consisting of Oic and P;
- $A_4$ is selected from the group consisting of D-alanine (a) and D-serine (s); and
- $A_5$ is selected from the group consisting of L-[para-methyl]-phenylalanine(F(p-me)), L-[para-bromo]-phenylalanine(F(p-Br)), L-[para-iodo]-phenylalanine(F(p-I)), and L-[para-nitro]-phenylalanine F(p-NO$_2$)).

2. The compound of claim 1 that comprises at least one blocking group.

3. The compound of claim 2 that is amidated at a C-terminus.

4. The compound of claim 1 that consists of $A_1$-$A_2$-$A_3$-$A_4$-$A_5$.

5. The compound of claim 4 selected from the group consisting of rOicPGF, rOicPaF(p-Me), rOicPsF(p-Me), rOicPaF(p-Br), rOicPaF(p-I) and rOicPaF(p-NO$_2$).

6. The compound of claim 1 comprising a formula selected from the group consisting of rOicPGF, rOicPaF(p-Me), rOicPsF(p-Me), rOicPaF(p-Br), rOicPaF(p-I) and rOicPaF(p-NO$_2$).

7. The compound of claim 6 comprising the formula rOicPaF(p-Me) or rOicPsF(p-Me).

8. A method of inhibiting thrombin-induced platelet aggregation comprising administering an effective amount of a compound of claim 1 to platelets.

9. A method of inhibiting a thrombin-mediated activity comprising administering an effective amount of a compound of claim 1 to a cell.

10. The method of claim 9 wherein the activity is coagulation.

11. The method of claim 10 wherein the activity is platelet aggregation.

12. The method of claim 9 wherein the activity is cell motility.

13. The method of claim 12 wherein said cell is a cancer cell.

14. The method of claim 9 wherein the activity is cell adhesion.

15. The method of claim 9 wherein the activity is calcium mobilization.

16. A method of inhibiting thrombin activation of mammalian cells having thrombin receptors, said method comprising contacting said cells with an effective amount of a compound of claim 1.

17. The method of claim 16 wherein said compound comprises a sequence selected from the group consisting of rOicPGF, rOicPaF(p-Me), r OicPsF(p-Me), rOicPaF(p-Br), rOicPaF(p-I) and rOicPaF(p-NO$_2$).

18. A method of inhibiting thrombin-induced platelet activation, platelet aggregation or thrombosis in a mammal comprising administering an effective amount of a compound of claim 1 to said mammal.

19. The method of claim 18 wherein said mammal is a human.

20. A pharmaceutical composition comprising a compound of claim 1, and optionally at least one pharmaceutically acceptable carrier or excipient.

21. The composition of claim 20 comprising rOicPaF(p-Me).

22. A method of treating acute coronary syndrome in an individual in need thereof comprising administering an effective amount of a compound of claim 1.

23. The method of claim 22 wherein said compound is administered orally.

24. The compound of claim 1 wherein $A_1$-$A_2$-$A_3$-$A_4$-$A_5$ is located at the N-terminus of the peptide.

25. A method of inhibiting a thrombin-mediated activity comprising administering an effective amount of a compound of claim 24 to a cell.

26. The method of claim 25 wherein said compound is administered orally.

27. A compound of formula MAP4-$A_1$-$A_2$-$A_3$-$A_4$-$A_5$,
wherein MAP4 is a four-branched peptide consisting of a β-alanine core with a single lysine attached at its amino terminal end followed by two additional lysines;

$A_1$ is selected from the group consisting of D-arginine (r) and L-arginine (R);

$A_2$ is selected from the group consisting of (2S, 3aS, 7aS)-octahydroindole-2-carboxlic acid (Oic) and P;

$A_3$ is selected from the group consisting of Oic and P;

$A_4$ is selected from the group consisting of D-alanine (a) and D-serine (s); and $A_5$ is selected from the group consisting of L-[para-methyl]-phenylalanine(F(p-me)), L-[para-bromo]-phenylalanine(F(p-Br)), L-[para-iodo]-phenylalanine(F(p-I)), and L-[para-nitro]-phenylalanine F(p-NO$_2$)); and wherein at least one non-naturally occurring amino acid residue is present in $A_1$-$A_2$-$A_3$-$A_4$-$A_5$.

28. A method of inhibiting a thrombin-mediated activity comprising administering an effective amount of a compound of claim 26 to a cell.

29. The method of claim 28 wherein said compound is administered orally.

30. The compound of claim 1 that is an inhibitor of at least one thrombin-mediated activity.

31. The compound of claim 30 wherein the activity is selected from the group consisting of thrombin-induced platelet aggregation, thrombin-induced calcium mobilization, thrombin-mediated coagulation, thrombin-induced cell motility and thrombin-induced cell adhesion.

32. The compound of claim 30 wherein the activity is thrombin-induced platelet aggregation.

33. The compound of claim 30 wherein the activity is thrombin-induced calcium mobilization.

34. The compound of claim 30 wherein the activity is thrombin-mediated coagulation.

35. The compound of claim 32 that is an inhibitor of thrombin-induced calcium mobilization.

36. The compound of claim 32 that is an inhibitor of thrombin-mediated coagulation.

37. The compound of claim 32 wherein the activity is thrombin-induced cell motility.

38. The compound of claim 32 wherein the activity is thrombin-induced cell adhesion.

* * * * *

SEQUENCE LISTING

```
<160> NUMBER OF SEQ ID NOS: 17

<210> SEQ ID NO 1
<211> LENGTH: 9
<212> TYPE: PRT
<213> ORGANISM: Homo sapiens

<400> SEQUENCE: 1

Arg Pro Pro Gly Phe Ser Pro Phe Arg
  1               5

<210> SEQ ID NO 2
<211> LENGTH: 6
<212> TYPE: PRT
```

-continued

<213> ORGANISM: Homo sapiens

<400> SEQUENCE: 2

Ser Phe Leu Leu Arg Asn
 1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Ala Thr Leu Asp Pro Arg Ser Phe Leu Leu Arg
 1               5                  10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Pro Pro Gly Phe
 1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Pro Pro Gly
 1

<210> SEQ ID NO 6
<211> LENGTH: 12
<212> TYPE: PRT
<213> ORGANISM: Homo sapiens

<400> SEQUENCE: 6

Asp Lys Tyr Glu Pro Phe Trp Glu Asp Glu Glu Lys
 1               5                  10

<210> SEQ ID NO 7
<211> LENGTH: 4
<212> TYPE: PRT
<213> ORGANISM: Homo sapiens

<400> SEQUENCE: 7

Leu Asp Pro Arg
 1

<210> SEQ ID NO 8
<211> LENGTH: 5
<212> TYPE: PRT
<213> ORGANISM: Homo sapiens

<400> SEQUENCE: 8

-continued

Leu Pro Ala Pro Arg
 1               5

<210> SEQ ID NO 9
<211> LENGTH: 12
<212> TYPE: PRT
<213> ORGANISM: Homo sapiens

<400> SEQUENCE: 9

Ser Ile Leu Pro Ala Pro Arg Gly Tyr Pro Gly Gln
 1               5                  10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Pro Pro Gly Cys
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Pro Arg Pro Gly
 1               5

<210> SEQ ID NO 12
<211> LENGTH: 4
<212> TYPE: PRT
<213> ORGANISM: Homo sapiens

<400> SEQUENCE: 12

Pro Arg Ser Phe
 1

<210> SEQ ID NO 13
<211> LENGTH: 74
<212> TYPE: PRT
<213> ORGANISM: Homo sapiens

<400> SEQUENCE: 13

Ala Arg Arg Pro Glu Ser Lys Ala Thr Asn Ala Thr Leu Asp Pro Arg
 1               5                  10                  15

Ser Phe Leu Leu Arg Asn Pro Asn Asp Lys Tyr Glu Pro Phe Trp Glu
                20                  25                  30

Asp Glu Glu Lys Asn Glu Ser Gly Leu Thr Glu Tyr Arg Leu Val Ser
        35                  40                  45

Ile Asn Lys Ser Ser Pro Leu Gln Lys Gln Leu Pro Ala Phe Ile Ser
    50                  55                  60

Glu Asp Ala Ser Gly Tyr Leu Thr Ser Ser
 65                  70

<210> SEQ ID NO 14
<211> LENGTH: 61

```
<212> TYPE: PRT
<213> ORGANISM: Homo sapiens

<400> SEQUENCE: 14

Gly Gly Thr Gln Thr Pro Ser Val Tyr Asp Glu Ser Gly Ser Thr Gly
 1               5                  10                  15

Gly Gly Asp Asp Ser Thr Pro Ser Ile Leu Pro Ala Pro Arg Gly Trp
                20                  25                  30

Pro Gly Gln Val Cys Ala Asn Asp Ser Asp Thr Leu Glu Leu Pro Asp
            35                  40                  45

Ser Ser Arg Ala Leu Leu Leu Gly Trp Val Pro Thr Arg
        50                  55                  60

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Pro Pro Gly Phe Lys
 1               5

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaattccata tgggcggcac ccagaccccc agcgtc                              36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccgctcgagt cacctggtgg gcacccagcc cagaag                              36
```